(12) United States Patent
Endo et al.

(10) Patent No.: US 10,747,798 B2
(45) Date of Patent: Aug. 18, 2020

(54) CONTROL METHOD, PROCESSING APPARATUS, AND RECORDING MEDIUM

(71) Applicant: Panasonic Intellectual Property Management Co., Ltd., Osaka (JP)

(72) Inventors: Mitsuru Endo, Osaka (JP); Noriaki Horii, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 246 days.

(21) Appl. No.: 15/356,779

(22) Filed: Nov. 21, 2016

(65) Prior Publication Data
US 2017/0161370 A1 Jun. 8, 2017

(30) Foreign Application Priority Data

Dec. 2, 2015 (JP) ................. 2015-236141

(51) Int. Cl.
| | |
|---|---|
| *G06T 11/60* | (2006.01) |
| *G06T 11/20* | (2006.01) |
| *G06F 16/30* | (2019.01) |
| *G06F 16/338* | (2019.01) |
| *G06F 16/29* | (2019.01) |
| *G06F 16/31* | (2019.01) |

(Continued)

(52) U.S. Cl.
CPC ............ *G06F 16/338* (2019.01); *G06F 16/29* (2019.01); *G06F 16/322* (2019.01);
(Continued)

(58) Field of Classification Search
CPC ......... G06F 17/30625; G06F 17/30684; G06F 17/30696; G06F 17/30241; G06F 16/3344;
(Continued)

(56) References Cited

U.S. PATENT DOCUMENTS

| 5,596,712 A | 1/1997 | Tsuyama et al. |
| 8,639,639 B2 * | 1/2014 | Jamil ................... G06K 9/6234 706/12 |

(Continued)

FOREIGN PATENT DOCUMENTS

| JP | 5-165853 A | 7/1993 |
| JP | 11-066085 A | 3/1999 |

(Continued)

OTHER PUBLICATIONS

The Extended European Search Report from the European Patent Office (EPO) dated Sep. 26, 2017 for the related European Patent Application No. 16200969.0.

*Primary Examiner* — Kuen S Lu
(74) *Attorney, Agent, or Firm* — Greenblum & Bernstein, P.L.C.

(57) ABSTRACT

A control method includes displaying a decision tree including nodes and leaves, the nodes corresponding to questions asking about presence or absence of symptoms, the leaves corresponding to illnesses, and performing a first display of the nodes, acquiring an inputted, by a user, answer to a presented question, determining the inputted answer to the presented question, if it is determined that the user has answered that a symptom corresponding to a first node is present, performing a second display of a second node directly linked to the first node and located in a lower level, and if it is determined that the user has answered that the symptom corresponding to the first node is absent, performing the second display of a third node directly linked to the first node and located in a lower level, the third node being different from the second node.

17 Claims, 15 Drawing Sheets

(51) Int. Cl.
*G06F 16/33* (2019.01)
*G16H 50/20* (2018.01)
*G16H 10/20* (2018.01)

(52) U.S. Cl.
CPC ........ *G06F 16/3344* (2019.01); *G06T 11/206* (2013.01); *G06T 11/60* (2013.01); *G16H 10/20* (2018.01); *G16H 50/20* (2018.01)

(58) Field of Classification Search
CPC ...... G06F 16/322; G06F 16/29; G06F 16/338; G06T 11/206; G06T 11/60; G16H 10/20; G16H 50/20
USPC ........................................................ 707/722
See application file for complete search history.

(56) References Cited

U.S. PATENT DOCUMENTS

| | | |
|---|---|---|
| 2002/0032878 A1 | 3/2002 | Karpf |
| 2003/0139946 A1* | 7/2003 | van Mierlo ............ G06Q 50/22 705/2 |
| 2003/0140063 A1 | 7/2003 | Pizzorno et al. |
| 2006/0030890 A1 | 2/2006 | Cosentino et al. |
| 2011/0314332 A1* | 12/2011 | Shimada .............. G06F 11/0709 714/26 |
| 2012/0109966 A1* | 5/2012 | Liang .................. G06F 16/3323 707/740 |
| 2012/0179699 A1* | 7/2012 | Ward .................. G06F 17/2258 707/754 |
| 2012/0290310 A1* | 11/2012 | Watson .................. G06Q 10/10 705/2 |
| 2013/0117280 A1 | 5/2013 | Donaldson et al. |
| 2015/0227701 A1 | 8/2015 | Nicolaas |

FOREIGN PATENT DOCUMENTS

| | | |
|---|---|---|
| JP | 2001-325104 | 11/2001 |
| JP | 2002-351492 A | 12/2002 |
| JP | 2003-263438 A | 9/2003 |
| JP | 2013-101226 A | 5/2013 |

* cited by examiner

|  | ILLNESS 1 | ILLNESS 2 | ILLNESS 3 | ILLNESS 4 |
|---|---|---|---|---|
| SYMPTOM A | ○ | ○ |  |  |
| SYMPTOM B | ○ |  | ○ |  |
| SYMPTOM C | ○ |  |  |  |
| SYMPTOM D |  | ○ |  |  |
| SYMPTOM E |  |  | ○ |  |
| SYMPTOM F |  |  |  | ○ |

FIG. 13

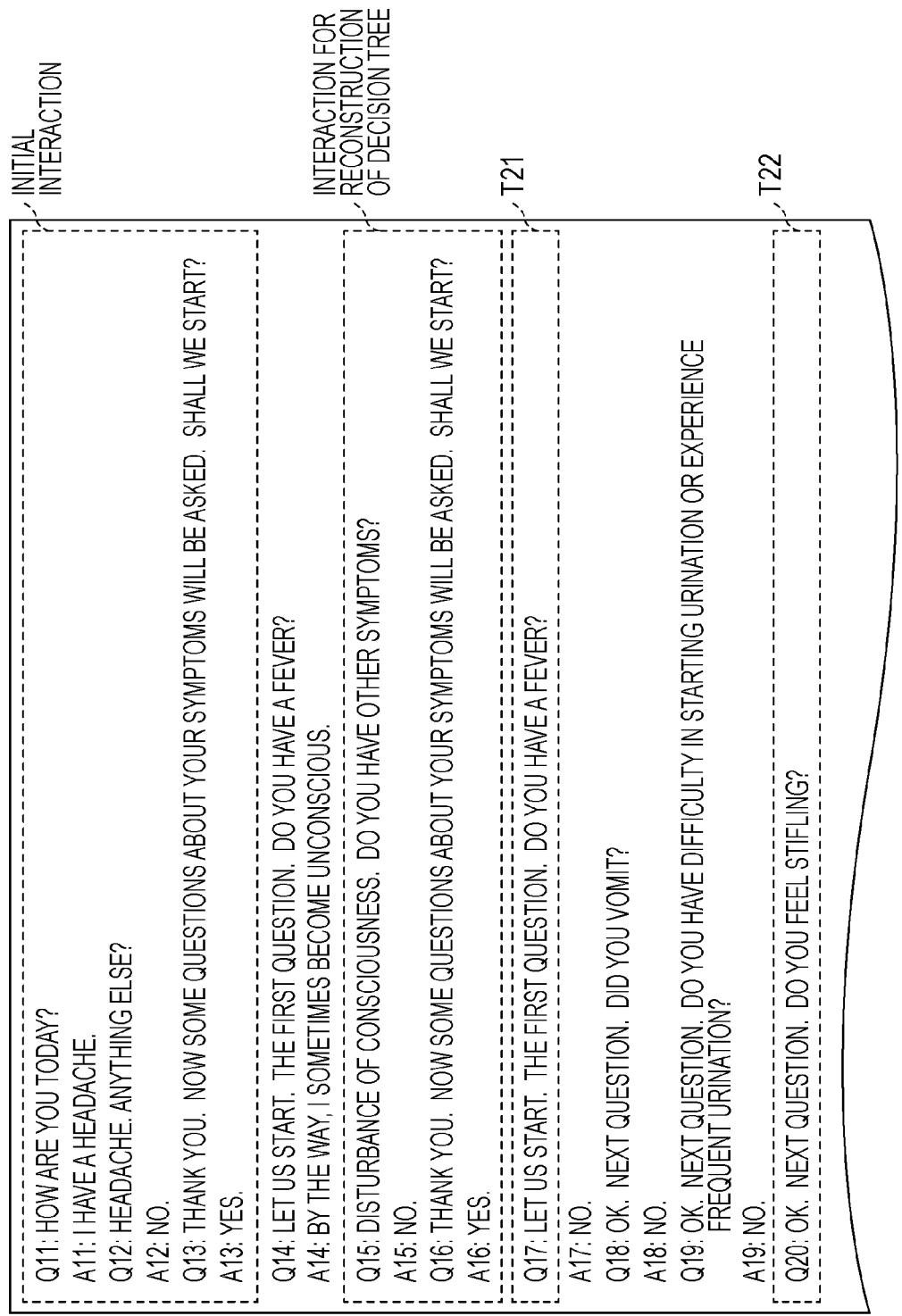

Q11: HOW ARE YOU TODAY?
A11: I HAVE A HEADACHE.
Q12: HEADACHE. ANYTHING ELSE?
A12: NO.
Q13: THANK YOU. NOW SOME QUESTIONS ABOUT YOUR SYMPTOMS WILL BE ASKED. SHALL WE START?
A13: YES.
— INITIAL INTERACTION

Q14: LET US START. THE FIRST QUESTION. DO YOU HAVE A FEVER?
A14: BY THE WAY, I SOMETIMES BECOME UNCONSCIOUS.
Q15: DISTURBANCE OF CONSCIOUSNESS. DO YOU HAVE OTHER SYMPTOMS?
A15: NO.
Q16: THANK YOU. NOW SOME QUESTIONS ABOUT YOUR SYMPTOMS WILL BE ASKED. SHALL WE START?
A16: YES.
— INTERACTION FOR RECONSTRUCTION OF DECISION TREE

Q17: LET US START. THE FIRST QUESTION. DO YOU HAVE A FEVER?
A17: NO.
Q18: OK. NEXT QUESTION. DID YOU VOMIT?
A18: NO.
Q19: OK. NEXT QUESTION. DO YOU HAVE DIFFICULTY IN STARTING URINATION OR EXPERIENCE FREQUENT URINATION?
A19: NO.
Q20: OK. NEXT QUESTION. DO YOU FEEL STIFLING?

— T21

— T22

|  | ILLNESS 1 | ILLNESS 2 | ILLNESS 3 | ILLNESS 4 |
|---|---|---|---|---|
| SERIOUSNESS | NOT HAVING | HAVING | NOT HAVING | NOT HAVING |
| SYMPTOM A | ○ | ○ |  |  |
| SYMPTOM B | ○ |  | ○ |  |
| SYMPTOM C | ○ |  |  |  |
| SYMPTOM D |  | ○ |  |  |
| SYMPTOM E |  |  | ○ |  |
| SYMPTOM F |  |  |  | ○ |

D2

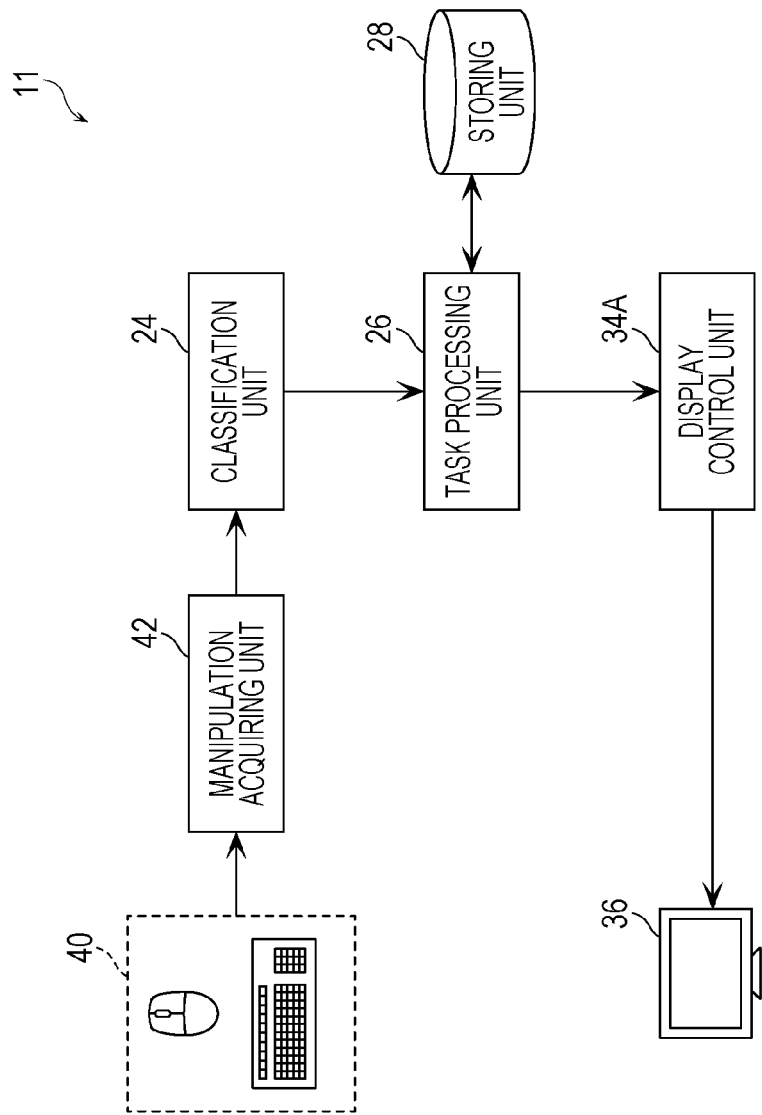

CONTROL METHOD, PROCESSING APPARATUS, AND RECORDING MEDIUM

BACKGROUND

1. Technical Field

The present disclosure relates to a control method, a processing apparatus, and a recording medium.

2. Description of the Related Art

In the related art, techniques and apparatuses that narrow down information through interactions by using classification trees are disclosed.

However, while answering sequential questions to identify desired information from among a plurality of pieces of predetermined information by using a technique and an apparatus of the related art, the respondent may feel anxious or irksome if there are a large number of questions before identification of the desired information.

In addition, if the respondent feels anxious or irksome, the respondent might not be in their regular state of mind, and correct answers might not be acquired. If correct answers are not acquired, it is necessary to search for information again, which increases the processing load and power consumption of the apparatus.

SUMMARY

In one general aspect, the techniques disclosed here feature a control method executed by a processor for controlling a display connected to the processor and a memory, the processor being connected to an input that receives an inputted answer to a presented question, the control method including: causing the display to display a decision tree, the decision tree being stored in the memory and including a plurality of nodes and a plurality of leaves, the plurality of nodes each corresponding to a question asking about presence or absence of a corresponding one of a plurality of symptoms, the plurality of leaves each corresponding to one of a plurality of illnesses, and to perform a first display of each of the plurality of nodes; acquiring the inputted answer to the presented question from the input, the inputted answer being input to the input by a user; determining an answer to the presented question from the inputted answer; if it is determined that the user has answered that a symptom corresponding to a first node is present, causing the display to perform a second display of a second node that is directly linked to at least the first node in the decision tree and is located in a lower level, the second display being different from the first display; and if it is determined that the user has answered that the symptom corresponding to the first node is absent, causing the display to perform the second display of a third node that is directly linked to at least the first node in the decision tree and is located in the lower level, the third node being different from the second node.

A control method according to an embodiment of the present disclosure can suppress a respondent's feeling of anxiety or irksomeness at the time of engaging in questions and answers in search of desired information.

It should be noted that general or specific embodiments may be implemented as a system, a method, an integrated circuit, a computer program, a recording medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 13 illustrates a second interaction example in the first embodiment;

FIG. 22 is a block diagram illustrating a configuration of a search support apparatus according to a third embodiment.

Figure 1:
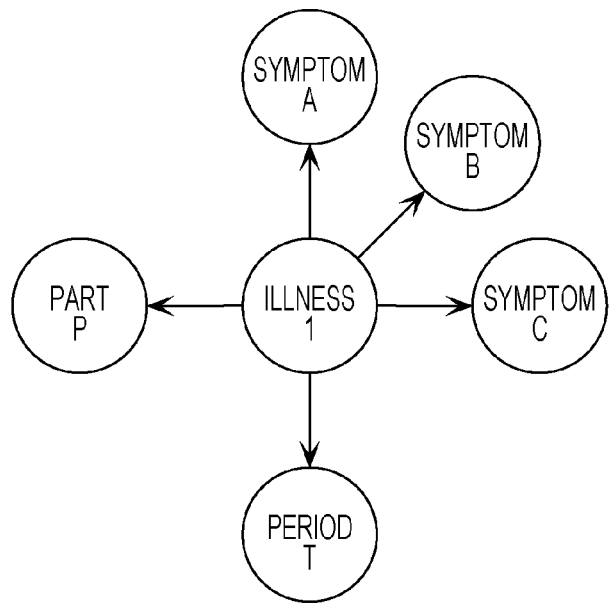
FIG. 1 is a first explanation diagram used to describe a method for identifying an illness on the basis of checking of symptoms.

DETAILED DESCRIPTION (1) A control method according to an aspect of the present disclosure is a control method executed by a processor for controlling a display connected to the processor and a memory, the processor being connected to an input that receives an inputted answer to a presented question, the control method including: causing the display to display a decision tree, the decision tree being stored in a memory and including a plurality of nodes and a plurality of leaves, the plurality of nodes each corresponding to a question asking about presence or absence of a corresponding one of a plurality of symptoms, the plurality of leaves each corresponding to one of a plurality of illnesses, and to perform a first display of each of the plurality of nodes; acquiring the inputted answer to the presented question from the input, the inputted answer being input to the input by a user; determining an answer to the presented question from the inputted answer; if it is determined that the user has answered that a symptom corresponding to a first node is present, causing the display to perform a second display of a second node that is directly linked to at least the first node in the decision tree and is located in a lower level, the second display being different from the first display; and if it is determined that the user has answered that the symptom corresponding to the first node is absent, causing the display to perform the second display of a third node that is directly linked to at least the first node in the decision tree and is located in the lower level, the third node being different from the second node.

According to the above aspect, the processing apparatus presents, to the user, a decision tree indicating a question that has already been presented and a question that may be presented later as nodes and changes the display mode of the decision tree in accordance with the progress of the search. By seeing the presented decision tree, the user can grasp the position of the question at the current time point in a series of questions in search of one piece of information. In addition, by seeing the change in the display mode of the presented decision tree, the user can know that the information search is being progressed. In the above manner, a processing apparatus can suppress a user's feeling of anxiety or irksomeness at the time of engaging in questions and answers in search of desired information. Unless the user feels anxious or irksome, it is unnecessary to search for information again as a result of the anxiety or irksomeness, thereby avoiding an increase in the processing load and consumption power of the apparatus.

(2) In the above aspect, a process may be repeated until the second node or the third node corresponds to one of the plurality of leaves, the process including causing the display to perform the second display, acquiring the inputted answer, determining the answer, causing the display to perform the first display of the second node or causing the display to perform the second display of the third node.

(3) In the above aspect, the second node may be arranged on a lower left of the first node and the third node is arranged on a lower right of the first node in the decision tree.

(4) In the above aspect, if it is determined that the user has answered that the symptom corresponding to the first node is present, the display may be caused to perform a third display of at least the third node in the decision tree, the third display being different from the first display and the second display, and if it is determined that the user has answered that the symptom corresponding to the first node is absent, the display may be caused to perform the third display of at least the second node in the decision tree.

(5) In the above aspect, the plurality of nodes may include one root, display may be caused to perform the second display of the root, the first node, and a node that is present between the root and the first node in the decision tree.

(6) In the above aspect, the second display may include emphasis and enlargement.

(7) In the above aspect, the third display may include deletion of display and grayscale display.

(8) In the above aspect, a number of levels of child nodes that are linked to the first node from the first node to the plurality of leaves may be counted, and the display may be caused to display the number of levels as a number of remaining questions.

(9) In the above aspect, the input device may include at least one of a microphone, a keyboard, and a touch panel.

(10) A control method according to another aspect of the present disclosure is a control method for controlling a display connected to a processor and a memory, the processor being connected to an input that receives an inputted answer to a presented question, the control method including: causing the display to display a decision tree, the decision tree being stored in a memory and including a plurality of nodes and a plurality of leaves, the plurality of nodes each corresponding to a question asking about necessity of a corresponding one of a plurality of real estate property conditions, the plurality of leaves each corresponding to one of a plurality of real estate properties, and to perform a first display of each of the plurality of nodes; causing the display to perform the first display of a first node corresponding to the presented question; acquiring the inputted answer to the presented question from the input, the inputted answer being input to the input by a user; determining an answer to the presented question from the inputted answer; if it is determined that the user has answered that a real estate property condition corresponding to the first node is necessary, causing the display to perform a second display of the first node and the second display of a second node that is directly linked to the first node in the decision tree and is located in a lower level, the second display being different from the first display; and if it is determined that the user has answered that the real estate property condition corresponding to the first node is unnecessary, causing the display to perform a third display of the first node and the second display of a third node that is directly linked to the first node in the decision tree and is located in the lower level, the third node being different from the second node.

(11) A control method according to another aspect of the present disclosure is a control method for controlling a display connected to a processor and a memory, the processor being connected to an input that receives an inputted answer to a presented question, the control method including: causing the display to display a decision tree, the decision tree being stored in a memory and including a plurality of nodes and a plurality of leaves, the plurality of nodes each corresponding to a question asking about necessity of a corresponding one of a plurality of itinerary conditions, the plurality of leaves each corresponding to one of a plurality of itineraries, and to perform a first display of each of the plurality of nodes; causing the display to perform the first display of a first node corresponding to the presented question; acquiring the inputted answer to the presented question from the input, the inputted answer being input to the input by a user; determining an answer to the presented question from the inputted answer; if it is determined that the user has answered that an itinerary condition corresponding to the first node is necessary, causing the display to perform a second display of the first node and the second display of a second node that is directly linked to the first node in the decision tree and is located in a lower level, the second display being different from the first display; and if it is determined that the user has answered that the itinerary condition corresponding to the first node is unnecessary, causing the display to perform a third display of the first node and the second display of a third node that is directly linked to the first node in the decision tree and is located in the lower level, the third node being different from the second node.

(12) A control method according to another aspect of the present disclosure is a control method for controlling a display connected to a processor and a memory, the processor being connected to an input that receives an inputted answer to a presented question, the control method including: causing the display to display a decision tree, the decision tree being stored in a memory and including a plurality of nodes and a plurality of leaves, the plurality of nodes each corresponding to a question asking about presence or absence of a corresponding one of a plurality of fault conditions in a predetermined apparatus, the plurality of leaves each corresponding to one of a plurality of remedial measures for fault conditions in the predetermined apparatus, and to perform a first display of each of the plurality of nodes; causing the display to perform the first display of a first node corresponding to the presented question; acquiring the inputted answer to the presented question from the input, the inputted answer being input to the input by a user; determining an answer to the presented question from the inputted answer; if it is determined that the user has answered that a fault condition corresponding to the first node is present, causing the display to perform a second display of the first node and the second display of a second node that is directly linked to the first node in the decision tree and is located in a lower level, the second display being different from the first display; and if it is determined that the user has answered that the fault condition corresponding to the first node is absent, causing the display to perform a third display of the first node and the second display of a third node that is directly linked to the first node in the decision tree and is located in the lower level, the third node being different from the second node.

It should be noted that general or specific aspects may be implemented as a system, a method, an integrated circuit, a computer program, a computer-readable recording medium such as a compact disk read only memory (CD-ROM), or any selective combination of a system, a method, an integrated circuit, a computer program, and a recording medium.

Embodiments will be specifically described below with reference to the drawings.

It should be noted that any of the following embodiments illustrates a general or specific example. The numerals, shapes, materials, components, the arrangement and connection of components, steps, the order of steps, and the like described in the following embodiments are exemplary and should not limit the present disclosure. In addition, among the components described in the following embodiments, components that are not included in the independent claim indicating the most generic concept are described as optional components.

First Embodiment

This embodiment describes a search support apparatus, a search support method, and the like that can suppress a respondent's (user's) feeling of anxiety or irksomeness at the time of engaging in questions and answers in search of desired information. It should be noted that this embodiment describes, as an example, a method for supporting the identification of an illness of a user who is exhibiting symptoms that are considered to be obvious symptoms (hereinafter also referred to simply as symptoms) of an illness by searching for the illness on the basis of the symptoms by using a search support apparatus or the like. However, the usage of the search support apparatus according to this embodiment is not limited to this example.

FIG. 1 is a first explanation diagram used to describe a method for identifying an illness on the basis of checking of symptoms. As illustrated in FIG. 1, an illness 1 is associated with symptoms A, B, and C of the illness 1, a part P at which the illness 1 occurs, and a period T (e.g., three days or a month) over which a person has the illness 1.

The related art (e.g., Japanese Unexamined Patent Application Publication No. 2001-325104) discloses a technique and an apparatus for identifying the illness 1 of a user through predetermined information processing on the basis of the fact that the user is exhibiting the symptoms A, B, and C. According to this technique, the user is asked sequential questions as to whether or not the user is exhibiting a plurality of symptoms including the symptoms A, B, and C, and on the basis of answers to these questions, an illness (illness 1) of the user is searched and identified from among a plurality of predetermined illnesses. However, if the number of the plurality of predetermined illnesses is large, a large number of questions are necessary. Specifically, in the case of about a thousand illnesses, if a search is performed by using a binary tree, the number of questions in the longest path of the tree is estimated to be ten or more.

If a large number of sequential questions are presented to the user, the user may feel anxious or irksome during answering the questions. If the user feels anxious or irksome, the user might not be in their regular state of mind, and correct answers might not be acquired. If correct answers are not acquired, it is necessary to search for information again, and the processing load and power consumption of the apparatus increase.

The search support apparatus and the search support method according to this embodiment can suppress the user's feeling of anxiety or irksomeness at the time of engaging in questions and answers in search of desired information.

Figure 2:
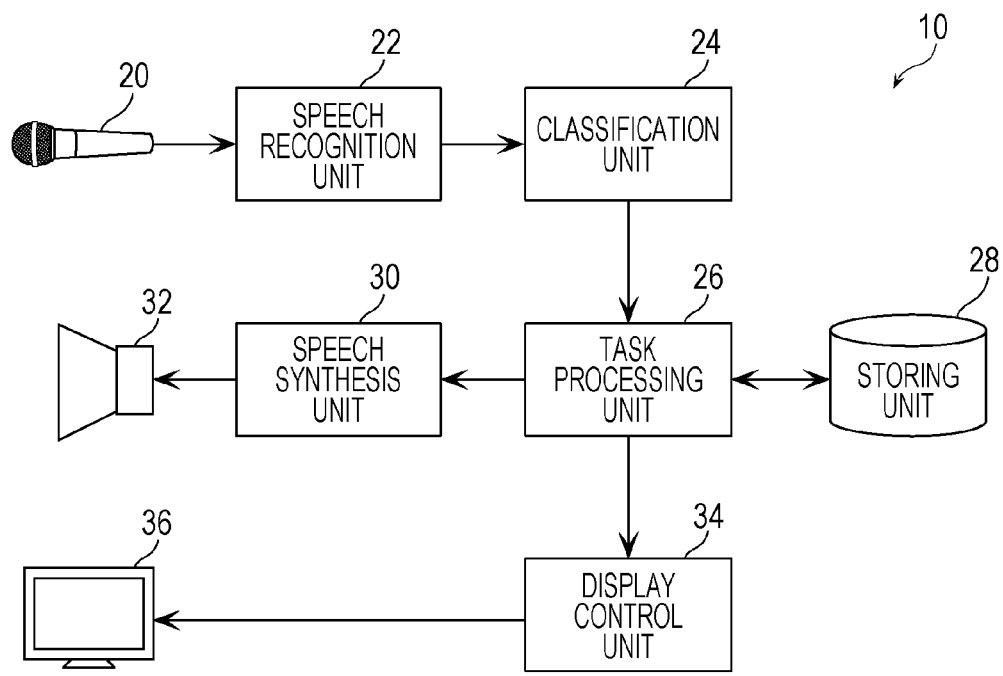
FIG. 2 is a block diagram illustrating a configuration of a search support apparatus according to a first embodiment.

FIG. 2 is a block diagram illustrating a configuration of a search support apparatus 10 according to this embodiment. The search support apparatus 10 is a search support apparatus that supports a search for one piece of information among a plurality of pieces of predetermined information. In the following description, the set of a question presented by the search support apparatus 10 to a user and a user's answer to the question is also referred to as an interaction.

As illustrated in FIG. 2, the search support apparatus 10 includes a microphone 20, a speech recognition unit 22, a classification unit 24, a task processing unit 26, a storage unit 28, a speech synthesis unit 30, a speaker 32, a display control unit 34, and a display device 36. It should be noted that the search support apparatus 10 may be configured in such a manner that the above components are contained in a single housing or that the above components are arranged to be dispersed and connected to each other via a network or the like so that communication can be performed.

The microphone 20 is a sound pickup device that picks up peripheral sounds to generate electric signals corresponding to the picked up sounds.

The speech recognition unit 22 is a processing unit that acquires the electric signals generated by the microphone 20 and that recognizes speech contained in the sounds picked up by the microphone 20 to generate text data. An example of the text data generated by the speech recognition unit 22 is data that can be represented by a character string, such as "I HAVE A FEVER" or "YES". It should be noted that the text data does not have a meaning of the character string. That is, "FEVER" contained in the text data is not associated with "fever" that means a high temperature or with a word having another meaning.

The classification unit 24 is a processing unit that acquires the text data generated by the speech recognition unit 22 to assign a meaning and classify the meaning. The classification unit 24 acquires, for example, "I HAVE A FEVER" as text data from the speech recognition unit 22, and by referring to predetermined interaction data, identifies this text data as an expression "I have a fever" meaning that the person has a high temperature (i.e., meaning is assigned). That is, at this time, a meaning of "fever" meaning a high temperature is assigned to "FEVER" contained in the text data, and "FEVER" is distinguished from a word having another meaning.

In addition, the classification unit 24 classifies text data in accordance with the meaning. Specifically, as the speech indicating that a person has a fever, in addition to the above expression "I have a fever", expressions such as "I got a fever" and "I feel hot" may be possible. The classification unit 24 classifies these expressions as a single meaning of having a fever. In the case where the classification unit 24 acquires "I DO" as text data from the speech recognition unit 22, it is difficult to assign a meaning only by using this text data. However, if the question that has been previously presented is known, the classification unit 24 can classify this expression by determining that it has a meaning of affirming the question. For example, in the case where text data "I DO" is acquired, if the question presented prior to acquiring the text data is "Do you have a fever?", the acquired text data "YES" or "I DO" is classified as a single meaning of Yes. In the above manner, the classification unit 24 deals with variations in expressions that may occur in the speech picked up by the microphone 20.

The task processing unit 26 is a processing unit that searches for the above-described one piece of information on the basis of interactions with the user. Specifically, the task processing unit 26 is a processing unit that acquires text data to which a meaning has been assigned and which has been subjected to meaning classification by the classification unit 24 to register the acquired text data in the storage unit 28. The task processing unit 26 manages the question that has been presented to the user or a plurality of questions to be presented to the user in the form of a decision tree. The task processing unit 26 determines whether or not it is possible to end the search for the desired information on the basis of the decision tree and information that has been acquired from the user up to the current time point. If it is determined that it is not possible to end the search for the desired information on the basis of the information that has been acquired up to the current time point, the task processing unit 26 decides the next question to be presented to the user and generates text data of the decided question. In addition, the task processing unit 26 causes the display device 36 to display the decision tree that the task processing unit 26 is managing and also changes the display mode of the decision tree depending on the interaction, i.e., the progress of the search. The structure of the decision tree and the display mode of the decision tree will be described later in detail.

The storage unit 28 is a storing device that stores various types of information. The storage unit 28 stores an illness data table, a keyword list, an exclusion list, and the like. The illness data table is a table indicating a plurality of predetermined illnesses in association with symptoms of the respective plurality of predetermined illnesses. The keyword list is a list indicating items for which the user has answered. The exclusion list is a list of items that are prohibited from being presented to the user among predetermined items. The above-described table and lists will be specifically described later with reference to examples.

The speech synthesis unit 30 is a processing unit that acquires text data of the next question to be presented to the user, the text data having been generated by the task processing unit 26, to generate electric signals of speech corresponding to this text data.

The speaker 32 is a sound output device that outputs a sound on the basis of the electric signals generated by the speech synthesis unit 30.

The display control unit 34 is a processing unit that generates image data of an image to be displayed on the display device 36 to provide the generated image data to the display device 36. The display control unit 34 acquires, from the task processing unit 26, information indicating the decision tree that the task processing unit 26 is managing and information indicating the display mode of the decision tree to generate image data of the decision tree to be displayed on the display device 36. Then, the display control unit 34 provides the generated image data to the display device 36.

The display device 36 is a display device that displays an image on the basis of image data provided from the display control unit 34.

It should be noted that each of the speech recognition unit 22, the classification unit 24, the task processing unit 26, the speech synthesis unit 30, and the display control unit 34 may be implemented by a processor executing a program or may be implemented by using a dedicated circuit.

Figures 3, 4:
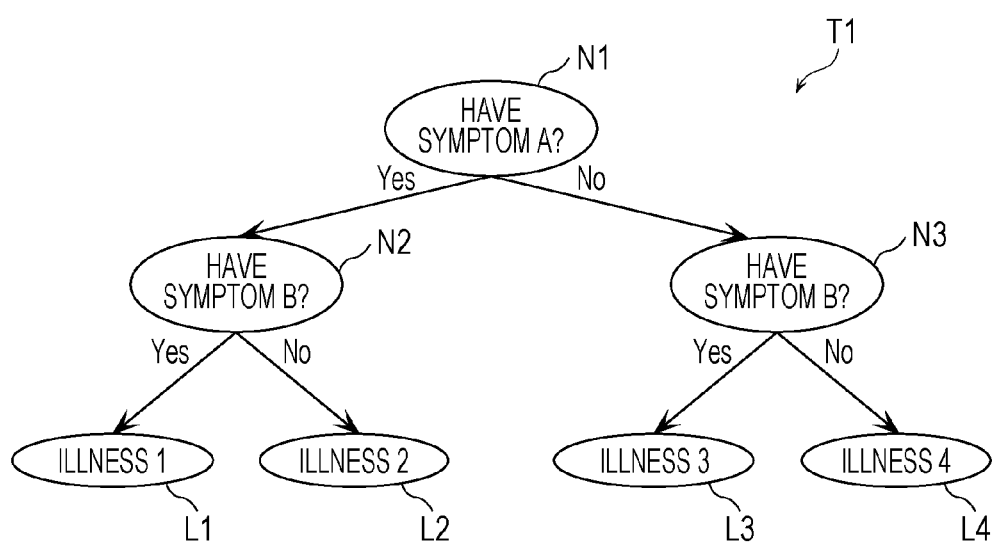
FIG. 3 illustrates data of illnesses in the first embodiment.
FIG. 4 illustrates a decision tree in the first embodiment.

FIG. 3 illustrates an illness data table D1 in this embodiment. The illness data table D1 is a table in which a plurality of illnesses and symptoms of the plurality of illnesses are associated with each other.

In the illness data table D1, each column indicates an illness, and circles in each row indicate the symptoms of a corresponding illness. For example, it is indicated that a person having the illness 1 exhibits the symptoms A, B, and C and that a person having an illness 2 exhibits the symptom A and a symptom D.

FIG. 4 illustrates a decision tree T1 in the first embodiment. The decision tree T1 is an exemplary decision tree for identifying one of the plurality of illnesses illustrated in FIG. 3 through sequential questions. With the decision tree T1, it is possible to search for the illness of a user among illnesses 1 to 4 on the basis of user's answers to two questions as to whether or not the user is exhibiting the symptom A and whether or not the user is exhibiting the symptom B.

It should be noted that the decision tree for identifying one of the plurality of illnesses illustrated in FIG. 3 is not limited to the decision tree T1 illustrated in FIG. 4 and may be another decision tree. Various studies have been done on the related art on how to create a decision tree for identifying each of a plurality of illnesses by using as few questions as possible. This embodiment may be implemented by using any type of decision tree.

The decision tree T1 illustrated in FIG. 4 has a data structure in the form of a tree including nodes N1, N2, and N3 and leaves L1, L2, L3, and L4. Each of the nodes N1, N2, and N3 is associated with a corresponding one or more questions for identifying one or more pieces of information including one of the plurality of predetermined illnesses. In addition, each of the leaves L1, L2, L3, and L4 is associated with a corresponding one of the plurality of predetermined illnesses.

The task processing unit 26 focuses on the nodes one by one from a root node (node N1) toward the leaves in the decision tree T1. The focused node is also referred to as a node of attention.

The task processing unit 26 presents a question corresponding to a node of attention to the user and acquires the user's answer to the presented question. Among child nodes of the node of attention, the task processing unit 26 sets a child node corresponding to the answer acquired from the user as a new node of attention and presents a question corresponding to the node of attention to the user. Upon reaching one of the leaves by repeating this process, the task processing unit 26 identifies the illness corresponding to the leaf as the illness of the user.

Specifically, by using the decision tree T1, with respect to the question as to whether the user is exhibiting the symptom A (node N1), the task processing unit 26 acquires an answer indicating that the symptom A is exhibited, i.e., an affirmative answer (Yes), or an answer indicating that the symptom A is not exhibited, i.e., a negative answer (No). Then, with respect to the question as to whether the user is exhibiting the symptom B (node N2 or N3), the task processing unit 26 acquires an answer indicating Yes or No. In the above manner, the task processing unit 26 identifies the illness of the user from among the illnesses 1 to 4 through a search.

It should be noted that in the decision tree T1, (a) among child nodes of each of the nodes contained in the decision tree T1, each child node corresponding to the next question to be presented if an affirmative answer to the question corresponding to the node is acquired, may be arranged in a predetermined direction with respect to the node, and (b) among child nodes of each of the nodes contained in the decision tree T1, each child node corresponding to the next question to be presented if a negative answer to the question corresponding to the node is acquired, may be arranged in a direction different from the predetermined direction with respect to the node. That is, in the decision tree T1, the task processing unit 26 may arrange a child node in the lower left of a single node, the child node corresponding to the next question to be presented if an answer indicating Yes to a question corresponding to the single node is acquired, and may arrange a child node in the lower right of the single node, the child node corresponding to the next question to be presented if an answer indicating No to the question is acquired. With such arrangement, the user who has seen this decision tree can intuitively grasp how the question and answers to this question are connected to each other in the decision tree.

Figure 5:
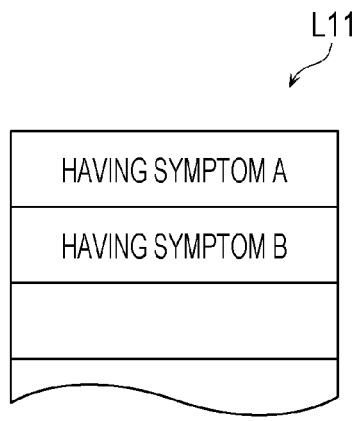
FIG. 5 illustrates a keyword list in the first embodiment.

FIG. 5 illustrates a keyword list L11 in this embodiment.

The keyword list L11 illustrated in FIG. 5 is a list in which information based on the user's answers is registered as keywords, the list being stored in the storage unit 28. Data in the keyword list L11 is cleared prior to initiating interactions between the search support apparatus 10 and the user. Then, keywords are registered in the keyword list L11 on the basis of answers acquired by the search support apparatus 10 from the user through interactions with the user. Specifically, text data acquired by the task processing unit 26 from the classification unit 24 is registered in the keyword list L11.

The keyword list L11 illustrated in FIG. 5 illustrates a keyword list obtained when, after an answer indicating "having symptom A" has been acquired from the user, an answer indicating that the user is exhibiting the symptom B is further acquired. The keyword list L11 is a list in which symptoms that the user is exhibiting and symptoms that the user is not exhibiting are sorted according to the user's answers, and registration of keywords in the keyword list L11 corresponds to transition of the node of attention from the root node toward the leaves in the decision tree.

It should be noted that, in the case where an answer indicating "Yes" has been acquired from the user to the presented question, the answer is handled as an answer affirming the presented question. That is, in the case where an answer indicating "Yes" is acquired from the user to the question "Do you have a symptom A?", a keyword "HAVING SYMPTOM A" is registered in the keyword list L11.

Figure 6:
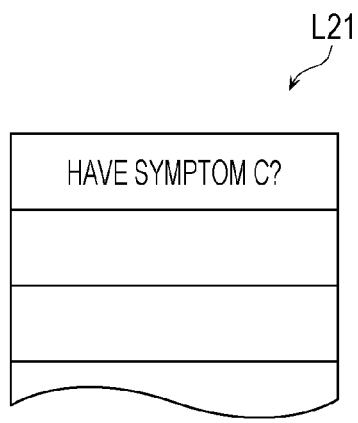
FIG. 6 illustrates an exclusion list in the first embodiment.

FIG. 6 illustrates an exclusion list L21 in this embodiment.

The exclusion list L21 illustrated in FIG. 6 is a list in which items are registered, the items being excluded from the items to be asked to the user, and is stored in the storage unit 28. Data in the exclusion list L21 is cleared prior to initiating interactions between the search support apparatus 10 and the user. Then, keywords are registered in the exclusion list L21 on the basis of answers acquired by the search support apparatus 10 from the user through interactions with the user. Specifically, the presented question is registered in the exclusion list L21 in the case where an answer from the user is included in neither candidate answers to the presented question nor candidate answers to other questions in the decision tree. Specifically, a keyword decided by the task processing unit 26 on the basis of the above-described condition is registered in the exclusion list L21. The exclusion list L21 is used at the time of reconstruction of the decision tree.

A process in a search support method executed by the search support apparatus 10 configured in the above manner will be described below.

Figure 7:
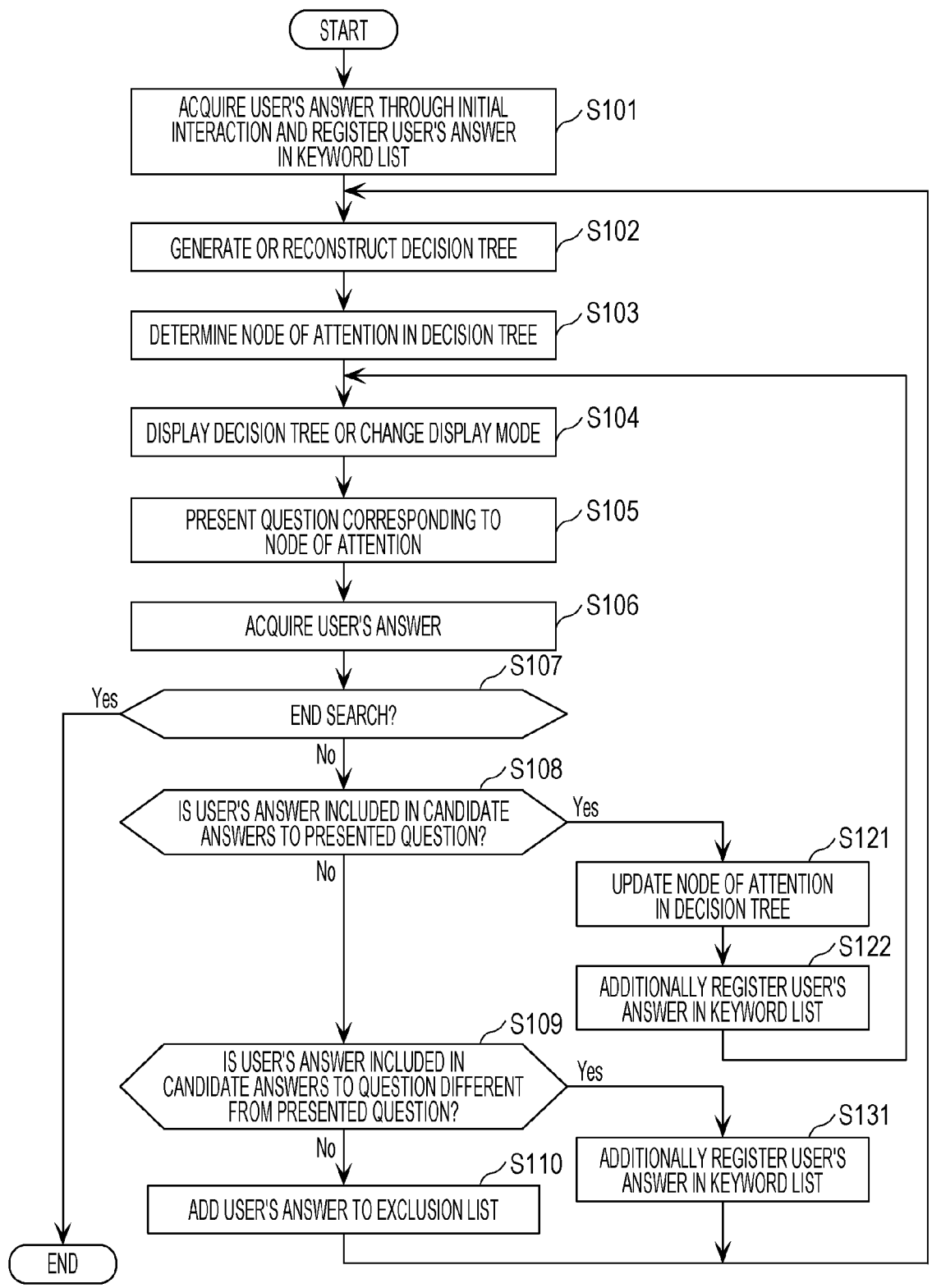
FIG. 7 is a flowchart illustrating a process flow in a search support method according to the first embodiment.

FIG. 7 is a flowchart illustrating a process flow in the search support method according to this embodiment.

Prior to performing a series of processing steps illustrated in FIG. 7, the search support apparatus 10 clears data in a keyword list stored in the storage unit 28. That is, at the time point of performing step S101, not a single keyword is registered in the keyword list.

In step S101, the task processing unit 26 performs an initial interaction with the user to acquire information on symptoms that the user is exhibiting to register the acquired information on the symptoms in a keyword list as keywords. The initial interaction means an interaction including the initial question that asks about symptoms that the user is exhibiting and a user's answer to the question. Through the initial interaction, the task processing unit 26 acquires information on one or more symptoms among the symptoms that the user is exhibiting. The task processing unit 26 acquires the information on one or more symptoms by, for example, receiving, by using the microphone 20, the words that the user has uttered by being asked about the symptoms exhibited, performing speech recognition by using the speech recognition unit 22, and by performing meaning classification by using the classification unit 24.

In step S102, the task processing unit 26 generates a decision tree on the basis of the initial keyword acquired in step S101. Various methods are possible as a method for generating the decision tree. One of the methods will be described below.

First, the task processing unit 26 generates, as a root node of the decision tree, a node corresponding to a question as to whether or not the user is exhibiting the symptom indicated by the initial keyword acquired in step S101.

Then, from among the pieces of data on illnesses that are kept in advance, the task processing unit 26 extracts data on all illnesses that cause the symptom corresponding to the keyword acquired in step S101 and selects one of the symptoms that are caused by about half the extracted illnesses. Then, the task processing unit 26 generates, as a child node of the root node, a node corresponding to a question as to whether or not the user is exhibiting the selected one of the symptoms. The child node of the root node is only this node. Candidate answers to this question are Yes (i.e., exhibiting the symptom) and No (i.e., not exhibiting the symptom). It should be noted that, at the time of selecting one of the symptoms, if there are a plurality of symptoms that are caused by about half the extracted one or more illnesses, an arbitrary one of the plurality of symptoms (e.g., the first one in the plurality of symptoms arranged in a predetermined order) is selected.

Then, from among the pieces of data on illnesses that are kept in advance, the task processing unit 26 extracts data on all illnesses that cause the symptom related to the question corresponding to the above-described child node and data on all illnesses that do not cause the symptom and performs the above-described process on the extracted data on the one or more illnesses, thereby generating child nodes of the child nodes (i.e., grandchild nodes of the root node). Child nodes are generated one by one in this manner, and when there is one illness that causes a symptom related to a question, a leaf corresponding to this illness is generated. Even if a node corresponds to two or more illnesses, if it is not possible to find a question that divides the illnesses into two groups: a group of illnesses that causes a symptom related to the question and a group of illnesses that do not cause the symptom, this node is set as a leaf without generating a child node.

With this method, a decision tree including, as leaves, all illnesses that cause the symptom corresponding to the keyword acquired in step S101 is generated.

It should be noted that in the case where step S102 is performed after performing step S110 or S131, which will be described later, a keyword in an exclusion list may have been registered in some cases. In this case, at the time of generating child nodes, by selecting a question corresponding to a child node from among questions excluding a question registered in the exclusion list, a new decision tree is generated.

In step S103, the task processing unit 26 decides a node of attention in the decision tree. In the case where this step is performed for the first time after the acquisition of the keyword in step S101, the one child node of the root node is set as the node of attention.

In step S104, the task processing unit 26 causes the display device 36 to display the decision tree generated in step S102 in a predetermined display mode under control of the display control unit 34. In addition, in the case where the task processing unit 26 has already caused the display device 36 to display the decision tree, the task processing unit 26 changes the display mode of the displayed decision tree to a predetermined display mode. When the display mode of the decision tree is changed, the display mode of the decision tree may be changed by changing the display mode of a node corresponding to the question for which an answer has been acquired from the user to a predetermined display mode indicating that the search has been progressed. In addition, among one or more nodes, a node for which an answer to the question corresponding to the node has been acquired and a subtree having the node as a vertex may be displayed. Alternatively, among one or more nodes, a node for which an answer to the question corresponding to the node has been acquired and a subtree having the node as a vertex may be displayed in a display mode that is different from that of the portions other than the node and the subtree in the decision tree.

In step S105, the task processing unit 26 presents a question corresponding to the node of attention to the user. Although various methods may be possible to present the question, there is a method of, for example, outputting text data of the question as speech by using the speech synthesis unit 30 and the speaker 32. It should be noted that the question may be presented to the user with the decision tree generated in step S102 displayed on the display device 36. In this case, the user can answer the presented question by grasping the position thereof in a series of questions.

In step S106, the task processing unit 26 acquires a user's answer. The microphone 20 receives the words uttered by the user after the question has been presented to the user in step S105, the speech recognition unit 22 recognizes the speech, and the classification unit 24 classifies the meaning, whereby the user's answer is acquired. It should be noted that in the case where it is not possible to acquire a user's answer even when a predetermined period passes after the question has been presented to the user in step S105, the process proceeds on the assumption that an answer indicating that there is no valid answer to the question has been acquired.

In step S107, on the basis of the user's answer acquired in step S106, the task processing unit 26 determines whether or not the information search is to end. Specifically, on the basis of the user's answer acquired in step S106, the task processing unit 26 performs the determination by determining whether or not the process has reached a leaf, that is, whether or not there are no more questions in the decision tree. If there are no more questions, it is determined that the information search is to end. If it is determined in step S107 that the information search is to end (Yes in step S107), the series of processing steps end. On the other hand, if it is determined in step S107 that the search for information is not to end (No in step S107), the process proceeds to step S108.

In step S108, the task processing unit 26 determines whether or not the user's answer acquired in step S106 is included in the candidate answers to the question presented in step S105. If it is determined that the user's answer acquired in step S106 is included in the candidate answers to the question (Yes in step S108), the process proceeds to step S121. On the other hand, if it is determined that the user's answer acquired in step S106 is not included in the candidate answers to the question (No in step S108), the process proceeds to step S109. It should be noted that in the case where an answer indicating that there is no valid answer to the question has been acquired in step S106, it is determined that the user's answer acquired in step S106 is not included in the candidate answers to the question.

In step S109, the task processing unit 26 determines whether or not the user's answer acquired in step S106 is included in the candidate answers to the other questions excluding the question presented in step S105 from the questions included in the decision tree. If it is determined in step S109 that the user's answer is included in the candidate answers to the other questions (Yes in step S109), the process proceeds to step S131. On the other hand, if it is determined in step S109 that the user's answer is not included in the candidate answers to the other questions (No in step S109), the process proceeds to step S110.

In step S110, the task processing unit 26 registers the question presented in step S105 in the exclusion list. Then, the process proceeds to step S102.

In step S121, the task processing unit 26 updates the node of attention in the decision tree. Specifically, the task processing unit 26 updates the node of attention in such a manner that, among child nodes of the node of attention at the current time point, a child node corresponding to the answer acquired in step S106 is set as a new node of attention.

In step S122, the task processing unit 26 registers the user's answer acquired in step S106 in the keyword list. Then, the process proceeds to step S104.

In step S131, the task processing unit 26 registers the user's answer acquired in step S106 to the keyword list. Then, the process proceeds to step S102.

Through the above-described series of processing steps, the search support apparatus 10 has interactions with the user while causing the display device 36 to display the decision tree and changing the display mode of the displayed decision tree on the basis of answers acquired from the user. Accordingly, the search support apparatus 10 can suppress the user's feeling of anxiety or irksomeness at the time of engaging in questions and answers in search of desired information.

Operations of the search support apparatus 10 will be described below with reference to two specific examples of interactions. A first interaction example corresponds to an exemplary case where the user provides an expected answer to a question presented by the search support apparatus 10 to the user. That is, the first interaction example corresponds to an exemplary case of Yes in step S108 in FIG. 7. A second interaction example corresponds to an exemplary case where the user provides an answer different from an expected answer to a question presented by the search support apparatus 10 to the user. That is, the second interaction example corresponds to an exemplary case of No in step S108 in FIG. 7 followed by Yes in step S109.

Figure 8:
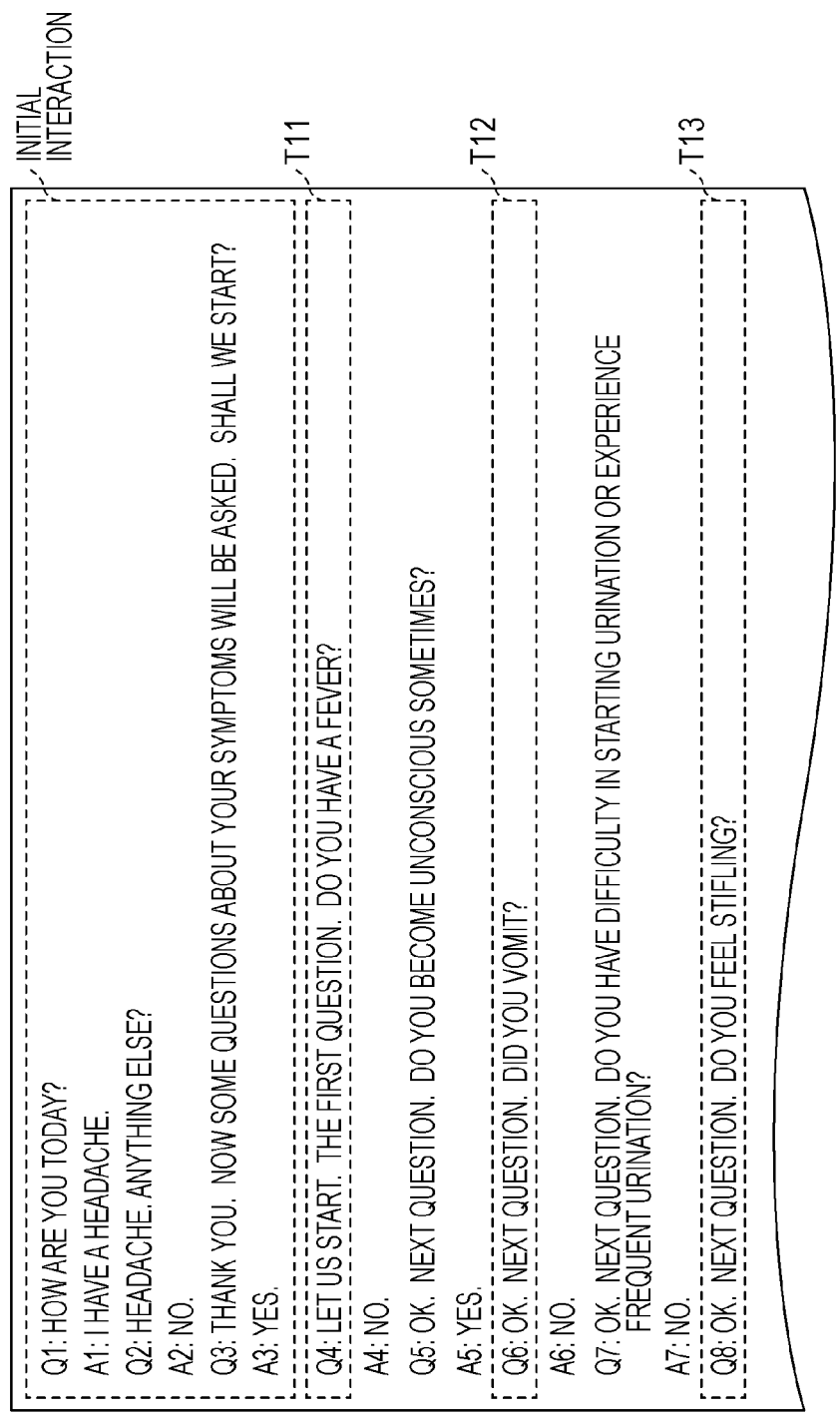
FIG. 8 illustrates a first conversion example in the first embodiment.

FIG. 8 illustrates the first interaction example in this embodiment. The interactions illustrated in FIG. 8 indicate contents of interactions through which a user exhibiting certain symptoms identifies the illness that causes the symptoms by using the search support apparatus 10. It should be noted that FIG. 8 illustrates the contents of speech made by the search support apparatus 10 as "Q (questioner)" and the contents of speech made by the user as "A (respondent)". A decision tree and a keyword list obtained at time points T11, T12, and T13 in this series of interactions will be described.

First, the search support apparatus 10 attempts to acquire symptoms that the user is exhibiting through an initial interaction (speeches Q1 to A3).

In the initial interaction, the search support apparatus 10 asks about the symptoms that the user is exhibiting by saying "HOW ARE YOU TODAY?" to the user (speech Q1). The user provides an answer to the question, the answer indicating that the user has a headache, "I HAVE A HEADACHE" (speech A1). On the basis of the user's answer, the search support apparatus 10 registers a keyword indicating that the user has a headache, specifically "HAVING HEADACHE", in a keyword list (step S101). After asking the user if the user has other symptoms, the search support apparatus 10 ends the initial interaction (speech Q2 to A3).

Upon completion of the initial interaction, on the basis of information on the user's symptom acquired through the initial interaction, that is, the keyword registered in the keyword list at this time, the search support apparatus 10 generates a decision tree and decides a node of attention in the decision tree (steps S102 and S103).

Then, the search support apparatus 10 displays the decision tree and also asks a first question, "DO YOU HAVE A FEVER?" (steps S104 and S105, speech Q4). This time point is set as the time point T11.

Upon a user's answer (speech A4) to the question presented by the search support apparatus 10, in accordance with the answer, the search support apparatus 10 updates the node of attention in the decision tree (step S121), continues asking sequential questions (speeches Q5 to Q8), and changes the display mode of the decision tree in a sequential manner on the basis of the user's answers (speeches A5 to A7). Time points of the speeches Q6 and Q8 are set as the time points T12 and T13, respectively.

Figure 9A:
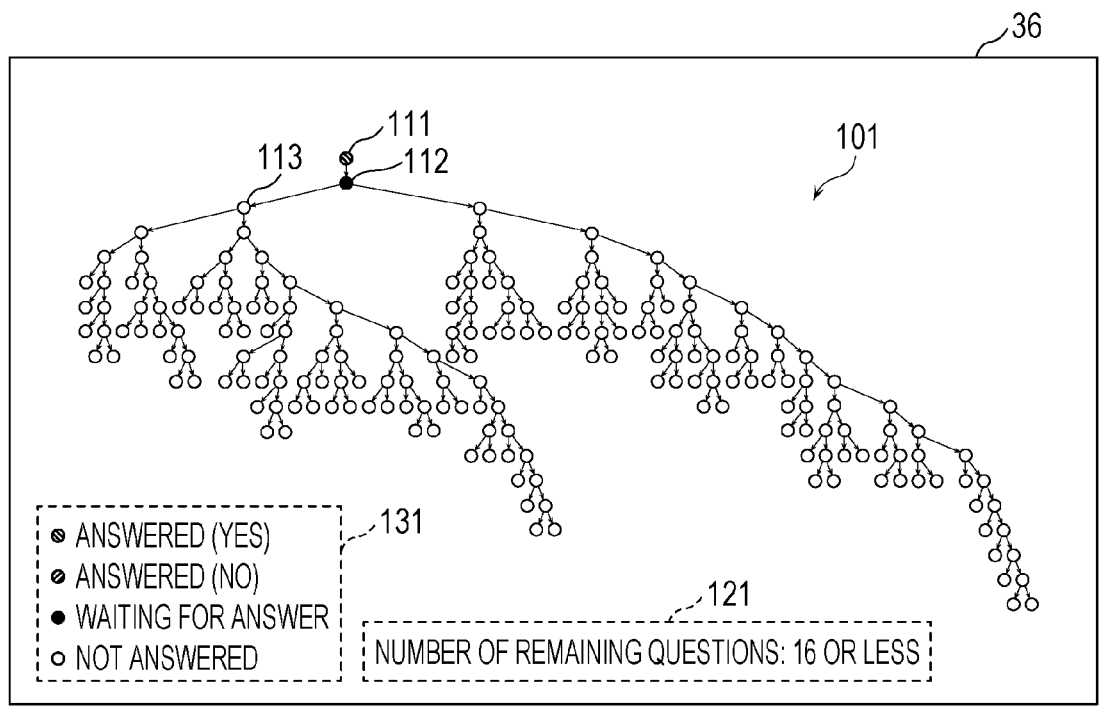
FIG. 9A illustrates a decision tree displayed on a display device at a first time point in the first interaction example in the first embodiment.
Figure 9B:
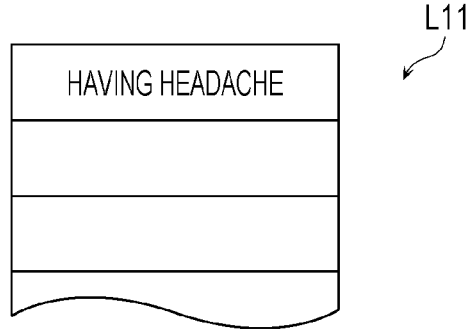
FIG. 9B illustrates a keyword list obtained at the first time point in the first conversion example in the first embodiment.

FIG. 9A illustrates a decision tree displayed on the display device 36 at the time point T11 in the first interaction example in this embodiment. FIG. 9B illustrates a keyword list obtained at the time point T11 in the first interaction example in this embodiment.

As illustrated in FIG. 9A, at the time point T11, the display control unit 34 causes the display device 36 to display a decision tree 101. A node 111 serving as a root node (the uppermost node in the figure) of the decision tree 101 is a node corresponding to a symptom of "having a headache". A node 112 is a node corresponding to a question that has been asked to the user and is waiting for an answer from the user, the node corresponding to a symptom of "having a fever". A node 113 is a node corresponding to a question yet to be presented to the user. In addition, the display control unit 34 causes the display device 36 to display a number of remaining questions 121 and explanatory notes 131 of display modes of the nodes. The number of remaining questions 121 is calculated by subtracting 1 from the levels of the subtree having, as a vertex, a node corresponding to a question for which an answer has been acquired at the latest time among the questions for which answers have been already acquired in the decision tree.

In addition, as illustrated in FIG. 9B, at the time point T11, "HAVING HEADACHE" is registered as a keyword in the keyword list L11. This is obtained from the user's answer (speech A2) in the initial interaction.

In this manner, since the position of the question at the current time point in a series of questions is displayed on the display device 36, the search support apparatus 10 can suppress the user's feeling of anxiety or irksomeness.

Next, two examples of decision trees displayed on the display device 36 at the time point T12 will be described.

Figure 10:
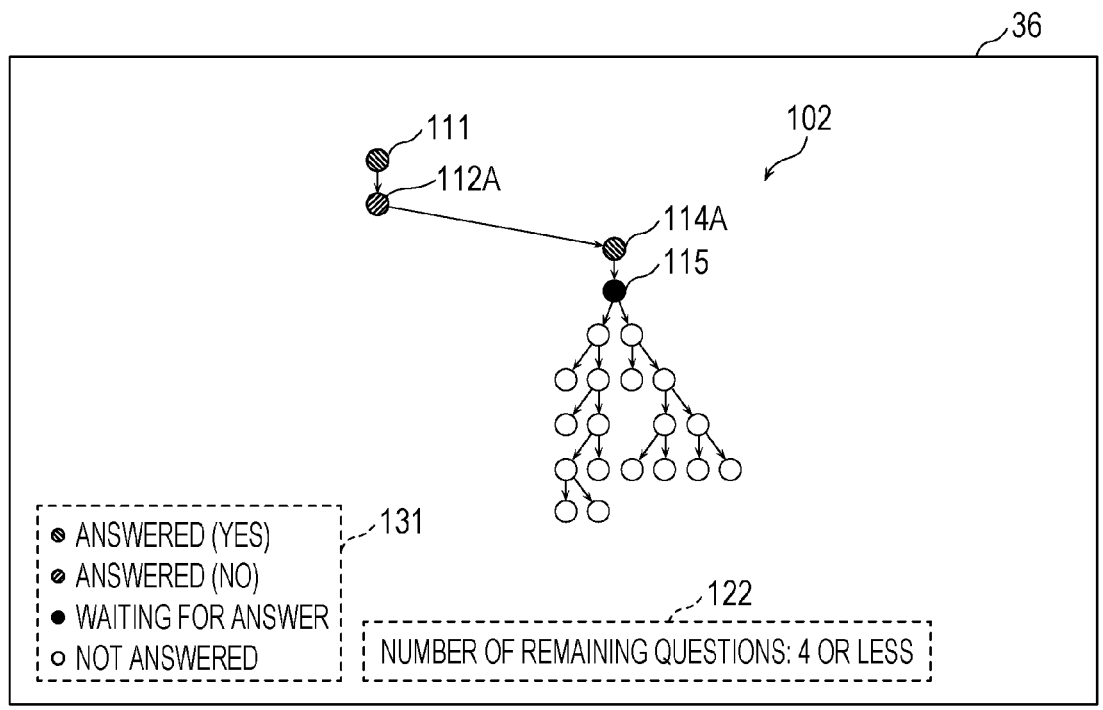
FIG. 10 illustrates a first example of a decision tree displayed on the display device at a second time point in the first interaction example in the first embodiment.

FIG. 10 illustrates a first exemplary decision tree displayed on the display device 36 at the time point T12 in the first interaction example in this embodiment.

A decision tree 102 illustrated in FIG. 10 is a decision tree displayed on the display device 36 at the time point T12. Specifically, the decision tree 102 includes nodes (nodes 111, 112A, and 114A) corresponding to questions for which answers have been acquired from the user through interactions up to the time point T12, a node (node 115) corresponding to a question that is waiting for an answer at the current time point, and nodes corresponding to questions that may be presented to the user after the current time point. The node 111 of the decision tree 102 is substantially the same (having the same keyword list obtained at this point) as the node 111 (FIG. 9A) of the decision tree 101. The nodes 112A and 114A in the decision tree 102 are displayed in display modes different from the display mode of the decision tree 101 in response to reception of an answer from the user.

The task processing unit 26 causes the display device 36 to display the decision tree 102 at the time point T12 by changing the display mode of the decision tree displayed on the display device 36 in accordance with the progress of interactions. It should be noted that the decision tree 102 may be enlarged or reduced in such a manner that the size of the decision tree 102 displayed on the display device 36 is included in a range of a predetermined size.

In addition, in the decision tree 102, the task processing unit 26 causes the display modes to be mutually different between the nodes corresponding to the questions for which answers have already been acquired from the user, the question that is waiting for an answer at the current time point, and the questions that may be presented later. More specifically, the nodes have different colors, sizes, shapes, patterns, or the like, the nodes are individually set to blink or not to blink, and the intervals of blinking are different, for example. With such configuration, the user can more appropriately grasp the above-described questions in the decision tree.

In accordance with the change in the display mode of the decision tree, the number of remaining questions 122 is updated.

Figure 11:
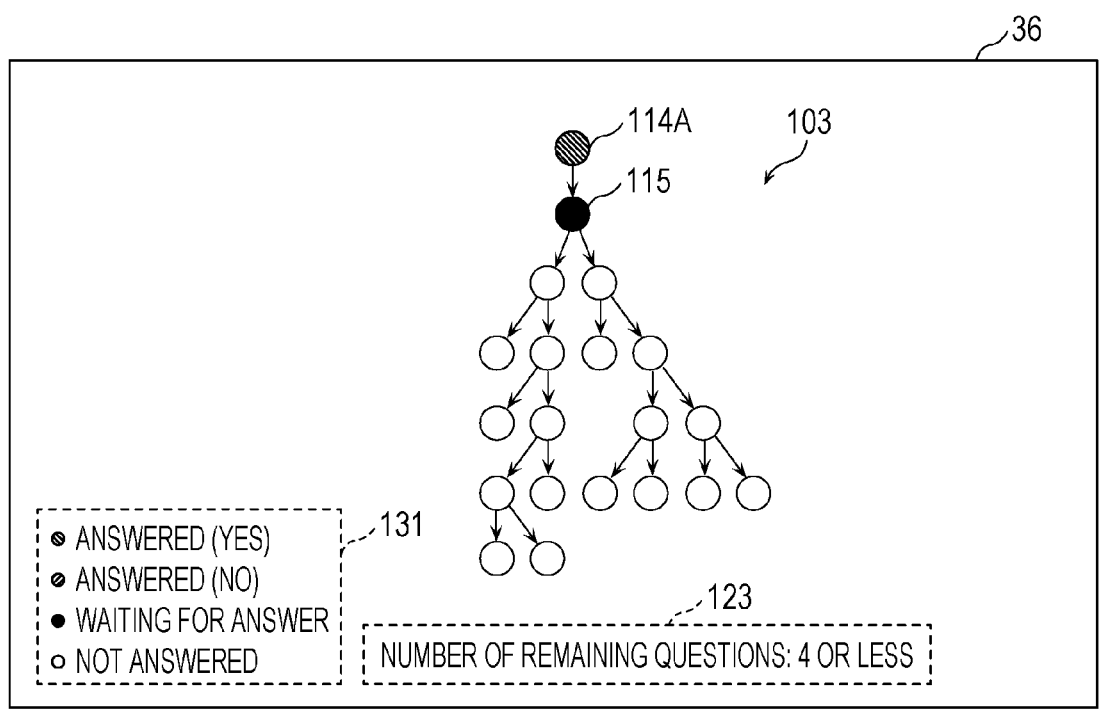
FIG. 11 illustrates a second example of a decision tree displayed on the display device at the second time point in the first interaction example in the first embodiment.

FIG. 11 illustrates a second exemplary decision tree displayed on the display device 36 at the time point T12 in the first interaction example in this embodiment.

A decision tree 103 illustrated in FIG. 11 is a decision tree displayed on the display device 36 at the time point T12. Specifically, the decision tree 103 includes a node (node 115) corresponding to a question that is waiting for an answer at the current time point and nodes corresponding to questions that may be presented after the current time point.

The decision tree 103 is different from the decision tree 102 in that the nodes (nodes 111, 112A, and 114A) corresponding to the questions for which answers from the user have been acquired through interactions up to the time point T12 are not included and in that the displayed decision tree is enlarged to have a larger size. The decision tree 103 has fewer nodes than the decision tree 102 because the above nodes are not included, and accordingly, the display size can be increased. A number of remaining questions 123 may be the same as the number of remaining questions 122. With such configuration, the user can more intuitively grasp the questions that are needed to be answered later.

It should be noted that the decision tree displayed on the display device 36 at the time point T12 may have the same display size as the decision tree 101 (FIG. 9A) in different display modes of the nodes.

Figure 12A:
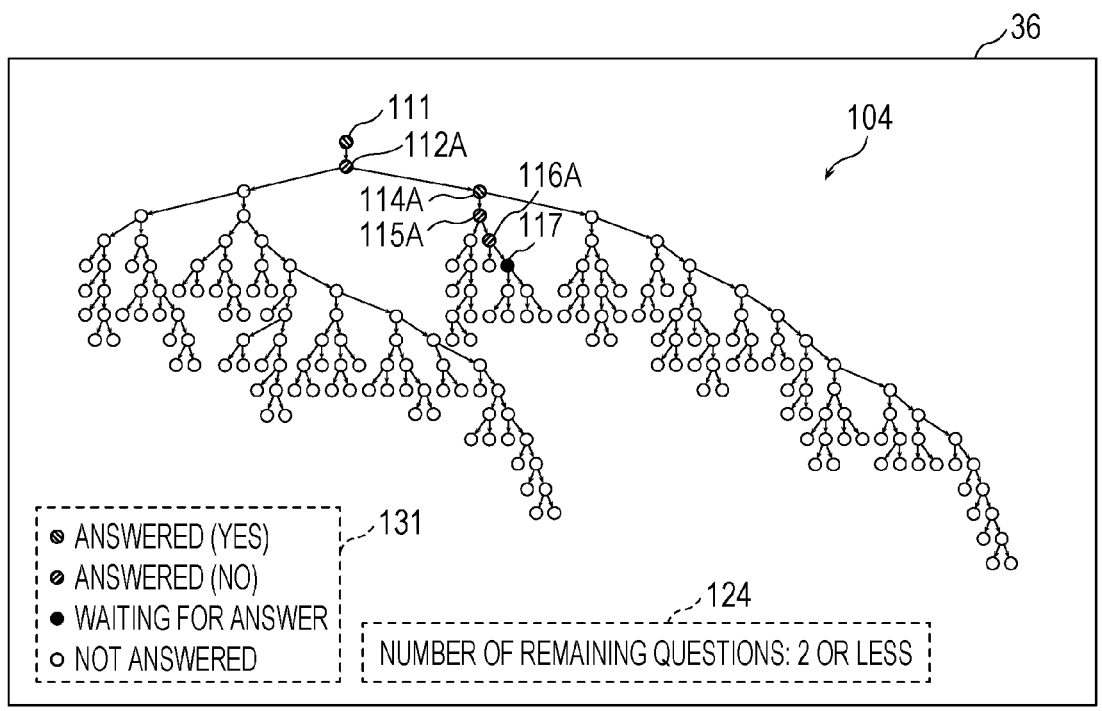
FIG. 12A illustrates a decision tree displayed on the display device at a third time point in the first interaction example in the first embodiment.
Figure 12B:
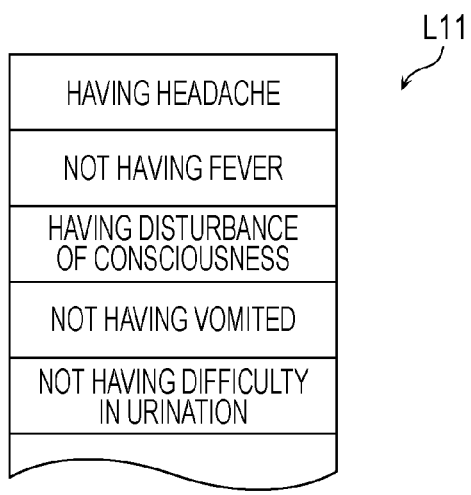
FIG. 12B illustrates a keyword list obtained at the third time point in the first conversion example in the first embodiment.

FIG. 12A illustrates a decision tree displayed on the display device 36 at the time point T12 in the first interaction example in this embodiment. FIG. 12B illustrates a keyword list obtained at the time point T13 in the first interaction example in this embodiment.

As illustrated in FIG. 12A, the display control unit 34 causes the display device 36 to display a decision tree 104 at the time point T12. A node 111 in the decision tree 104 is substantially the same (having the same keyword list obtained at this point) as the node 111 (FIG. 9A) in the decision tree 101. Although a node 112A is a node corresponding to the same question as the node 112 (FIG. 9A) in the decision tree 101, the display mode of the node 112A is changed on the basis of an answer received from the user. Nodes 114A, 115A, and 116A are each a node corresponding to a question to the user, and the display modes of the nodes 114A, 115A, and 116A are changed on the basis of the answers received from the user. A node 117 is a node corresponding to a question that has been asked to the user and is waiting for an answer from the user, the node corresponding to a symptom of "stifling". In addition, as in the case illustrated in FIG. 9, the display control unit 34 causes the display device 36 to display a number of remaining questions 124 and explanatory notes 131 of display modes of the nodes.

As illustrated in FIG. 12B, at the time point T13, information on the symptoms that the user is exhibiting or is not exhibiting, the data being obtained through interactions up to this time point, are registered in the keyword list L11 as keywords such as "HAVING HEADACHE" and "NOT HAVING FEVER".

In this manner, the search support apparatus 10 causes the display device 36 to display the decision tree and has interactions with the user while changing the display mode of the displayed decision tree on the basis of answers acquired from the user. Accordingly, the search support apparatus 10 can suppress the user's feeling of anxiety or irksomeness at the time of engaging in questions and answers in search of desired information.

FIG. 13 illustrates a second interaction example in this embodiment.

First, as in the case illustrated in FIG. 8, the search support apparatus 10 attempts to acquire information on symptoms that the user is exhibiting through an initial interaction (step S101, speeches Q11 to A13).

Upon completion of the initial interaction, as in the case illustrated in FIG. 8, the search support apparatus 10 generates a decision tree and decides a node of attention in the decision tree (steps S102 and S103).

Then, the search support apparatus 10 displays the decision tree and also asks a first question, "DO YOU HAVE A FEVER?" (steps S104 and S105, Q14). Expected candidate answers to this question is "Yes" indicating that the user has a fever and "No" indicating that the user does not have a fever.

In response, the user provides an answer, "I SOMETIMES BECOME UNCONSCIOUS", which is a different answer from any of the candidate answers (speech A14).

The task processing unit 26 determines that the above answer is not included in the candidate answers to the presented question (No in step S108), and then determines that the above answer is included in candidate answers to other questions excluding the presented question from the questions included in the decision tree (Yes in step S109). Then, the task processing unit 26 additionally registers the symptom "HAVING DISTURBANCE OF CONSCIOUSNESS" corresponding to the above answer in a keyword list (step S131), and, on the basis of the keyword list obtained after the registration, the task processing unit 26 reconstructs the decision tree and decides the node of attention in the decision tree (steps S102 and S103). This time point is a time point T21.

Upon the user's answer to the first question presented by the search support apparatus 10, in accordance with the answer, the search support apparatus 10 updates the node of attention in the decision tree (step S121) and continues asking sequential questions. A time point at which the search support apparatus 10 makes speech Q10, which is a question, is a time point T22.

Figure 14:
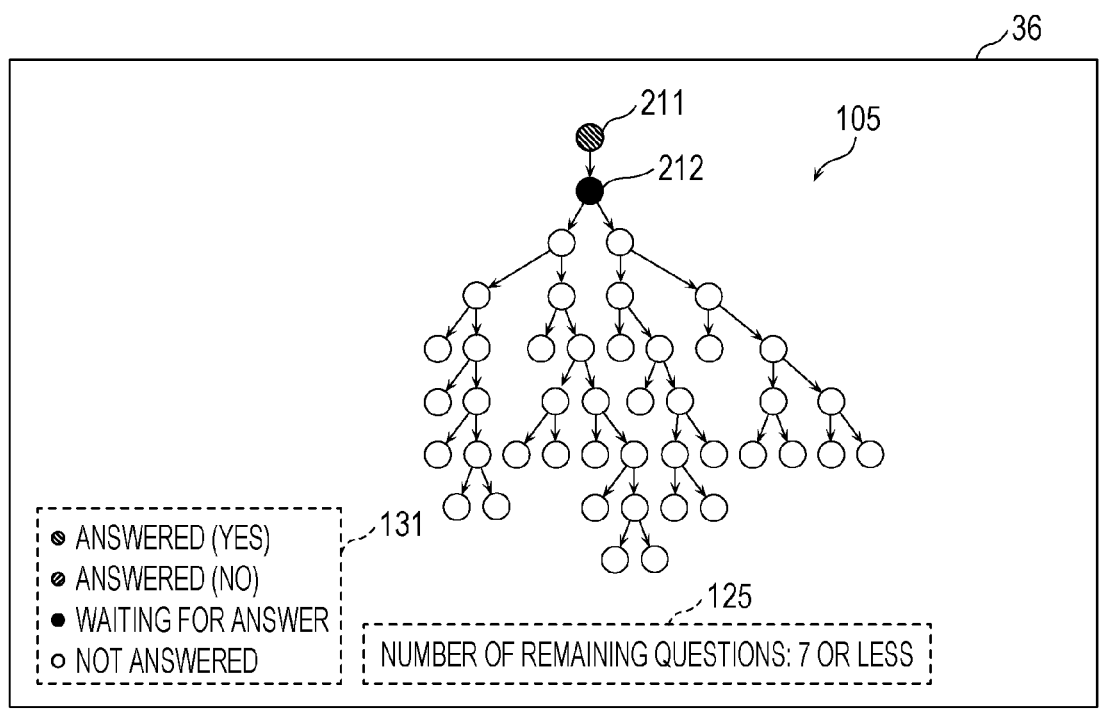
FIG. 14 illustrates a decision tree displayed at a first time point in the second interaction example in the first embodiment.
Figure 15:
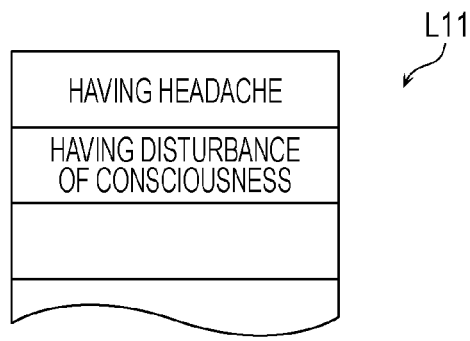
FIG. 15 illustrates a keyword list obtained at the first time point in the second interaction example in the first embodiment.

FIG. 14 illustrates a decision tree displayed at the time point T21 in the second interaction example in this embodiment. FIG. 15 illustrates a keyword list obtained at the time point T21 in the second interaction example in this embodiment.

As illustrated in FIG. 14, at the time point T21, the display control unit 34 causes the display device 36 to display a decision tree 105. A node 211 serving as a root node of the decision tree 105 is a node corresponding to a symptom of "having disturbance of consciousness". A node 212 is a node corresponding to a question that has been asked to the user and that is waiting for an answer from the user, the node corresponding to a symptom of "having a fever". In this manner, as a result of reconstruction of the decision tree, a decision tree is constructed in which information on the symptom registered in the keyword list at the time of reconstruction corresponds to the root node. In addition, a number of remaining questions 125 is updated on the basis of the reconstructed decision tree and the node of attention at the current time point.

In addition, as illustrated in FIG. 15, at the time point T21, "HAVING HEADACHE" and "HAVING DISTURBANCE OF CONSCIOUSNESS" are registered as keywords in the keyword list L11. These are obtained from the user's answers in the initial interaction and the following interactions.

Figure 16:
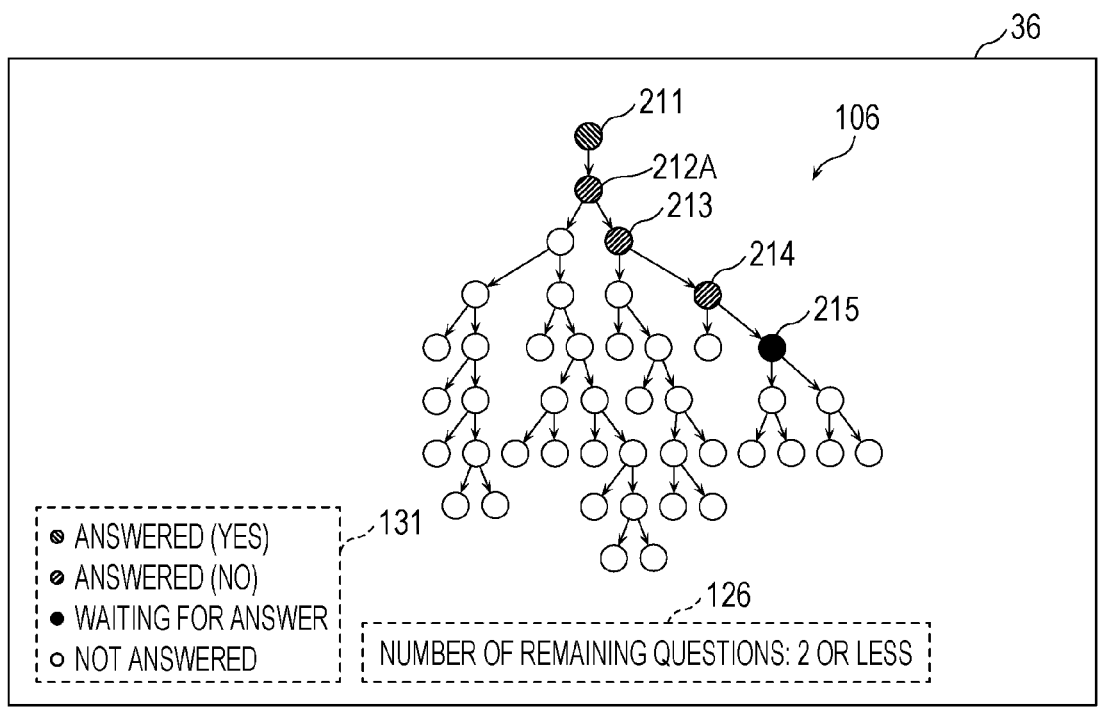
FIG. 16 illustrates a decision tree displayed at a second time point in the second interaction example in the first embodiment.
Figure 17:
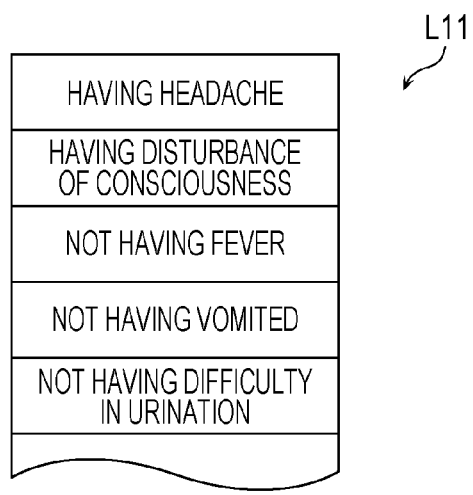
FIG. 17 illustrates a keyword list obtained at the second time point in the second interaction example in the first embodiment.

FIG. 16 illustrates a decision tree displayed at the time point T22 in the second interaction example in this embodiment. FIG. 17 illustrates a keyword list obtained at the time point T22 in the second interaction example in this embodiment.

As illustrated in FIG. 16, the display control unit 34 causes the display device 36 to display a decision tree 106 at the time point T22. A node 211 in the decision tree 106 is substantially the same (having the same keyword list obtained at this point) as the node 211 (FIG. 14) in the decision tree 105. Although a node 122A is a node corresponding to the same question as the node 212 (FIG. 14) in the decision tree 105, the display mode of the node 122A is changed on the basis of the answer received from the user. Nodes 213 and 214 are each a node corresponding to a question to the user, and the display modes of the nodes 213 and 214 are changed on the basis of the answers received from the user. A node 215 is a node corresponding a question that has been asked to the user and that is waiting for an answer from the user, the node corresponding to a symptom of "stifling". In addition, as in the case illustrated in FIG. 14, the display control unit 34 causes the display device 36 to display a number of remaining questions 126 and explanatory notes 131 of display modes of the nodes.

As illustrated in FIG. 17, at the time point T22, information on the symptoms that the user is exhibiting or is not exhibiting, the data being obtained through interactions up to this time point, are registered in the keyword list L11 as keywords such as "HAVING HEADACHE" and "HAVING DISTURBANCE OF CONSCIOUSNESS".

It should be noted that the case where the information handled by the search support apparatus 10 is information on illnesses and symptoms of illnesses has been described above. That is, in the above-described case, a plurality of pieces of predetermined information are a plurality of pieces of information indicating a plurality of predetermined illnesses, one piece of information is information indicating an illness of a user, and each of one or more nodes corresponds to a question as to whether or not the user is exhibiting a corresponding symptom caused by a corresponding one of the plurality of predetermined illnesses.

In addition, the search support apparatus 10 can handle the following information.

For example, the plurality of pieces of predetermined information may be a plurality of pieces of information indicating a plurality of real estate properties, the one piece of information may be information indicating a real estate property that the user desires, and each of the one or more nodes may correspond to a question as to whether or not the house rent of a corresponding real estate property, the distance from the nearest station, or the time it takes from the nearest station by walk satisfies desired conditions of the user.

In addition, the plurality of pieces of predetermined information may be a plurality of pieces of information indicating a plurality of itineraries, the one piece of information may be information indicating an itinerary that the user desires, and each of the one or more nodes may correspond to a question as to whether or not the purchase price of a corresponding itinerary, the destination, or the nights of stay satisfies desired conditions of the user.

Furthermore, the plurality of pieces of predetermined information may be a plurality of pieces of information indicating remedial measures for a plurality of fault conditions that may occur in a predetermined apparatus, the one piece of information may be information indicating a remedial measure for a fault condition that has occurred in a predetermined apparatus owned by a user, and each of the one or more nodes may correspond to a question as to whether or not the predetermined apparatus owned by the user exhibits a plurality of fault conditions.

As described above, the search support apparatus according to this embodiment presents, to the user, a decision tree including a questions that has already been presented and a question to be presented later and changes the display mode in accordance with the progress of the search. By seeing the presented decision tree, the user can grasp the position of the question at the current time point in a series of questions in search of the one piece of information. In addition, by seeing the change in the display mode of the presented decision tree, the user can know that the information search is being progressed. In this manner, it is possible to suppress the user's feeling of anxiety or irksomeness at the time of engaging in questions and answers in search of desired information. Unless the user feels anxious or irksome, it is unnecessary to search for information again as a result of the anxiety or irksomeness, thereby avoiding an increase in the processing load and power consumption of the apparatus.

Second Embodiment

This embodiment further describes a technique for display based on the property of search target information in a search support apparatus, a search support method, and the like that can suppress a respondent's feeling of anxiety or irksomeness at the time of engaging in questions and answers in search of desired information.

Figures 18, 19:
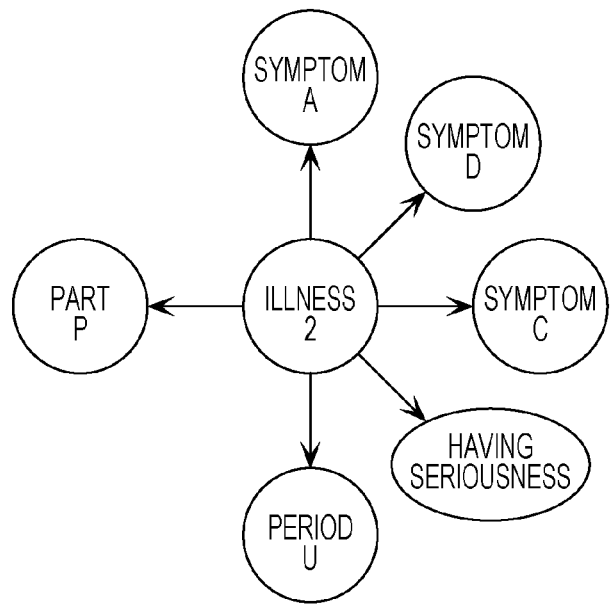
FIG. 18 is a second explanation diagram used to describe a method for identifying an illness on the basis of checking of accessory symptoms.
FIG. 19 illustrates a data table of illnesses in a second embodiment.

FIG. 18 is a second explanation diagram used to describe a method for identifying an illness on the basis of checking of obvious symptoms. As illustrated in FIG. 18, an illness 2 is associated with symptoms A, C, and D of the illness 2, a part P at which the illness 2 occurs, a period U over which a person has the illness 2, and the seriousness (degree of seriousness) of the illness 2. The association between the illness 2 and each item is different from the association between the illness 1 and each item in the first embodiment especially in that the seriousness of the illness 2 is associated.

The seriousness is an index indicating how serious an illness is. In this embodiment, illnesses are classified into serious illnesses and not serious illnesses, and then the illnesses classified as serious illnesses are associated with information indicating "having seriousness". It should be noted that the seriousness is an exemplary degree of importance indicating how important an illness is for a user.

A configuration of the search support apparatus in this embodiment is the same as or similar to the configuration of the search support apparatus 10 in the first embodiment.

FIG. 19 illustrates an illness data table D2 in this embodiment. The illness data table D2 is a table in which a plurality of illnesses and symptoms of the plurality of illnesses are associated with each other. The illness data table D2 indicates, in addition to the items indicated in the illness data table D1 in the first embodiment, "having seriousness" or "not having seriousness" as the seriousness of each of the illnesses. Specifically, illnesses 1, 3, and 4 do not have seriousness, and an illness 2 has seriousness.

Even if the symptoms that a person having a serious illness exhibits or does not exhibits are not completely the same as the symptoms that the user is exhibiting or is not exhibiting, in the case where the number of the symptoms that do not match is less than or equal to a predetermined number (e.g., one), the search support apparatus 10 according to this embodiment continues asking further questions.

Figure 20:
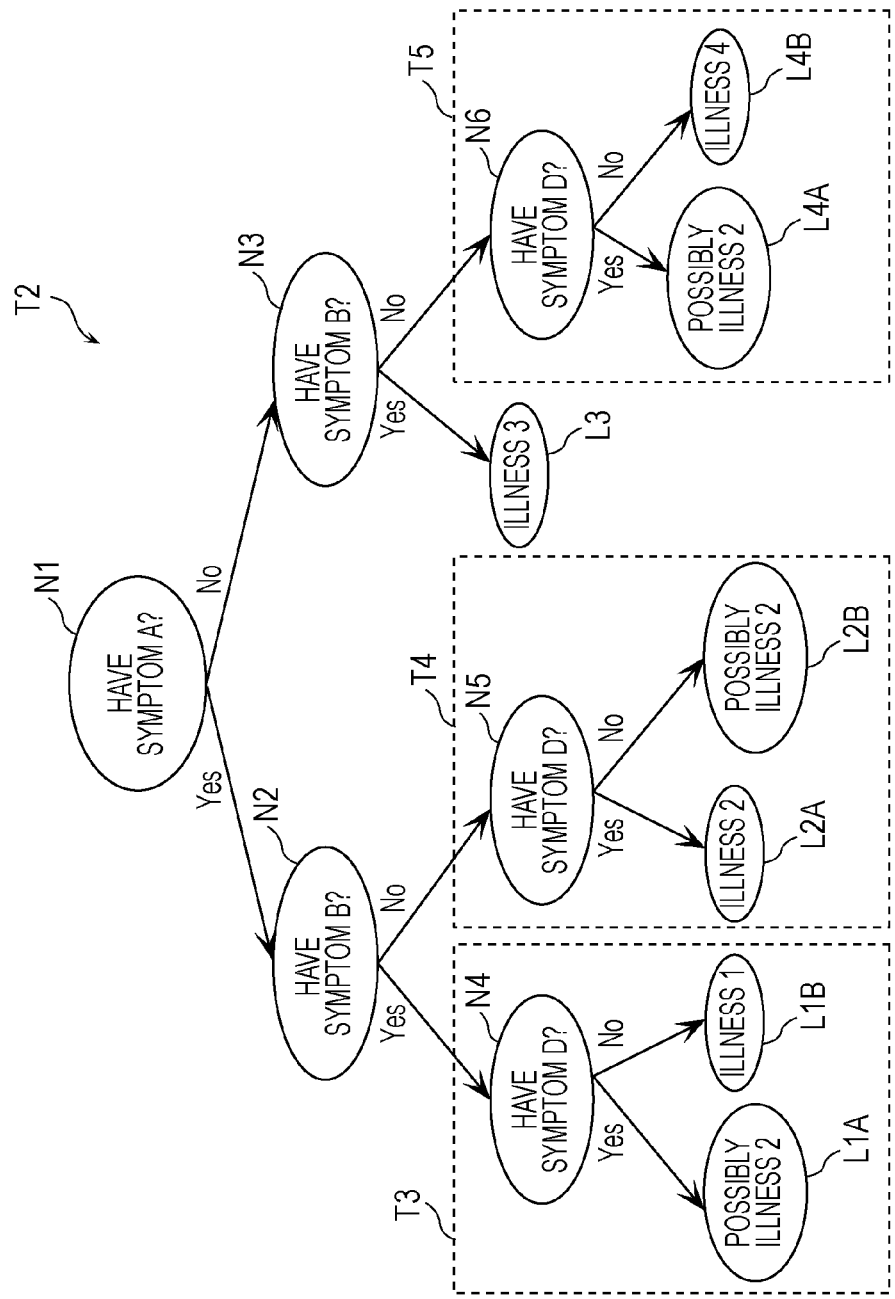
FIG. 20 illustrates a decision tree in the second embodiment.

FIG. 20 illustrates a decision tree T2 in this embodiment. The decision tree T2 is an exemplary decision tree for identifying the plurality of illnesses illustrated in FIG. 19 through sequential questions.

As in the decision tree T1 (FIG. 4) in the first embodiment, the decision tree T2 is a decision tree used to search for the illness of the user from among the illnesses 1 to 4. The decision tree T2 is different from the decision tree T1 in that the decision tree T2 includes additional decision trees (decision trees T3, T4, and T5) used to ask additional questions depending on the seriousness of the illness. The additional decision tree T3 includes a node N4 and leaves L1A and L1B. The additional decision tree T4 includes a node N5 and leaves L2A and L2B. The additional decision tree T5 includes a node N6 and leaves L3A and L3B. It should be noted that the nodes and leaves in the decision tree T2 that are substantially the same as those in the decision tree T1 are denoted by the same reference numerals.

From the illness data table D2, if the user is exhibiting the symptom A and is not exhibiting the symptom B, the illness of the user is identified as the illness 2. However, since the illness 2 is an illness having seriousness, even if it is difficult to determine that the user has the illness 2, it is desirable to present that the user possibly has the illness 2 in this case.

Accordingly, in a search support method according to this embodiment, in the above-described case, it is checked whether the user is exhibiting other symptoms (symptom C or D) whose presence or absence has not been known yet, and display is performed in accordance with the results of the check. Specifically, if the user is exhibiting the symptoms A and B, the decision tree T3 is further displayed, the decision tree T3 being an additional decision tree used to ask a question as to whether or not the user is exhibiting a symptom D, which is another symptom of the illness 2. In response to this question, if the user provides an answer indicating that the symptom D is exhibited, two symptoms out of three symptoms that a person having the illness 2 exhibits or does not exhibit are the same as the symptoms that the user is exhibiting or is not exhibiting. In this case, since there is a relatively high probability that the user has the illness 2, display is performed indicating that the user possibly has the illness 2 (leaf L1A). On the other hand, if the user provides an answer indicating that the symptom D is not exhibited, display is performed indicating that the user has the illness 1 (leaf L1B) as in the case where the decision tree T3 is not used (case of using the decision tree T1 in the first embodiment (FIG. 4)).

In addition, if the user is exhibiting the symptom A and is not exhibiting the symptom B, the decision tree T4 is further displayed, the decision tree T4 being an additional decision tree used to ask a question as to whether or not the user is exhibiting a symptom D, which is another symptom of the illness 2. In response to this question, if the user provides an answer indicating that the symptom D is exhibited, all of the above-described three symptoms are the same. In this case, since there is an extremely high probability that the user has the illness 2, display is performed indicating that the user has the illness 2 (leaf L2A). On the other hand, if the user provides an answer indicating that the symptom D is not exhibited, two symptoms out of the above-described three symptoms are the same. In this case, since there is a relatively high probability that the user has the illness 2, display is performed indicating that the user possibly has the illness 2 (leaf L2B).

It should be noted that a detailed description will be omitted here although the same description as the above description is applied to the decision tree T5.

Figure 21:
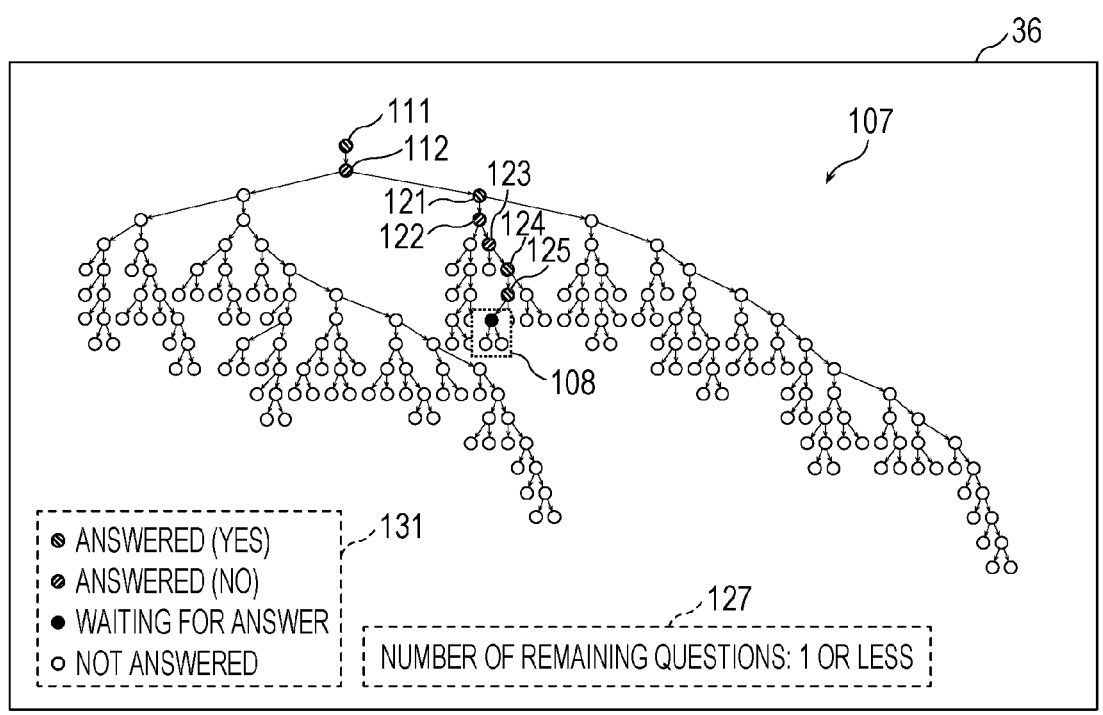
FIG. 21 illustrates a decision tree in interactions in the second embodiment.

FIG. 21 illustrates a decision tree 107 in interactions in this embodiment.

The decision tree 107 is used in the state where further interactions are performed from the state of the decision tree 104 (FIG. 12A) in the first embodiment. Specifically, in the case where the illness specified through interactions with the user is an illness having seriousness, the decision tree 107 asks an additional question and causes a decision tree 108 to be displayed, the decision tree 108 being an additional decision tree for the additional question.

In the above manner, if the searched one piece of information is of great importance, for example, the search support apparatus according to this embodiment can display an additional decision tree corresponding to a remaining question to acquire a user's answer. The user can also see the decision tree related to the remaining question. In the above manner, it is possible to suppress the user's feeling of anxiety or irksomeness.

Third Embodiment

This embodiment describes another configuration of the search support apparatus that can suppress a user's feeling of anxiety or irksomeness at the time of engaging in questions and answers in search of desired information.

FIG. 22 is a block diagram illustrating a configuration of a search support apparatus 11 according to this embodiment.

As illustrated in FIG. 22, the search support apparatus 11 according to this embodiment does not include the microphone 20, the speech recognition unit 22, the speech synthesis unit 30, and the speaker 32, which are included in the search support apparatus 10 in the first embodiment. Instead, the search support apparatus 11 includes a manipulation interface 40 and a manipulation acquiring unit 42. In addition, the search support apparatus 11 includes a display control unit 34A instead of the display control unit 34. It should be noted that the search support apparatus 11 may be configured in such a manner that the above components are contained in a single housing or that the above components are arranged to be dispersed and connected to each other via a network or the like so that communication can be performed, as in the first embodiment.

The manipulation interface 40 is a user interface for receiving manipulations made by the user on the search support apparatus 11. Specifically, the manipulation interface 40 is a mouse, a keyboard, a touch panel, or the like and receives clicking of a button, pressing of a key, movement of the mouse or a user's finger on the touch panel, or the like.

The manipulation acquiring unit 42 acquires the user's manipulations (e.g., the position selected on a screen and an input character string) received by the manipulation interface 40, and generates, on the basis of the acquired manipulations, text data as the user intends, to provide the text data to the classification unit 24.

The display control unit 34A has the function of the display control unit 34 and, in addition, causes the display device 36 to display a question to the user.

Accordingly, the search support apparatus 11 can cause the display device 36 to display a question to be presented to the user instead of having interactions by using speech and can receive an answer from the user to the question by using the manipulation interface 40, thereby having interactions with the user. Accordingly, the search support apparatus 11 can suppress the respondent's feeling of anxiety or irksomeness at the time of engaging in questions and answers in search of desired information.

It should be noted that in each of the above-described embodiments, each component may be implemented by configuring dedicated hardware or by executing a software program suitable for the component. Each component may also be implemented by a program executing unit, such as a central processing unit (CPU) or a processor reading out and executing a software program stored in a recording medium, such as a hard disk or semiconductor memory.

Although the embodiments of the search support apparatus and the like according to one or more aspects have been described above, the present disclosure is not limited to the above embodiments. An embodiment that is modified in various manners that a person skilled in the art will arrive at or an embodiment configured by a combination of components in different embodiments may also be included in the range of the one or more aspects without departing from the spirit of the present disclosure.

The present disclosure is applicable to a search support apparatus that can suppress a user's feeling of anxiety or irksomeness at the time of engaging in questions and answers in search of desired information. More specifically, the present disclosure is applicable to a search support apparatus that can suppress a user's feeling of anxiety or irksomeness in search of an illness, a real estate property, an itinerary, a remedial measure for a fault condition, or the like.

What is claimed is:

1. A control method executed by a processor for controlling a display connected to the processor and a memory, the processor being connected to an input that receives an inputted answer to a presented question, the control method comprising:
    causing the display to display a decision tree, the decision tree being stored in the memory and including a plurality of nodes and a plurality of leaves, the plurality of nodes each corresponding to a question asking about presence or absence of a corresponding one of a plurality of symptoms, the plurality of leaves each corresponding to one of a plurality of illnesses, and to perform a first display of each of the plurality of nodes at a first time point;
    acquiring the inputted answer to the presented question from the input, the inputted answer being input to the input by a user;
    determining an answer to the presented question from the inputted answer;
    if it is determined that the user has answered that a symptom corresponding to a first node is present, causing the display to perform, at a second time point later than the first time point, a second display of a second node that is directly linked to at least the first node in the decision tree and is located in a lower level, wherein a number of nodes being displayed in the second display is different from a number of nodes being displayed in the first display; and
    if it is determined that the user has answered that the symptom corresponding to the first node is absent, causing the display to perform the second display of a third node that is directly linked to at least the first node in the decision tree and is located in the lower level, the third node being different from the second node,
    wherein, if it is determined that the user's inputted answer is not included in candidate answers to the presented question, the method further comprising:
    determining that the inputted answer is included in candidate answers to other questions excluding the presented question from questions included in the decision tree;
    registering the user's inputted answer in a keyword list;
    changing a display mode of a node, corresponding to the question for which the user's inputted answer has been registered, to a predetermined display mode indicating that a search has been progressed; and
    reconstructing the decision tree based on the keyword list and the predetermined display mode by including a fourth node corresponding to the user's inputted answer, the fourth node being different from the first, second, and third nodes.

2. The control method according to claim 1, further comprising:
    repeating a process until the second node or the third node corresponds to one of the plurality of leaves, the process including causing the display to perform the second display, acquiring the inputted answer, determining the answer, causing the display to perform the first display of the second node or causing the display to perform the second display of the third node.

3. The control method according to claim 1, wherein the second node is arranged on a lower left of the first node and the third node is arranged on a lower right of the first node in the decision tree.

4. The control method according to claim 1, further comprising:
    if it is determined that the user has answered that the symptom corresponding to the first node is present, causing the display to perform a third display of at least the third node in the decision tree, the third display being different from the first display and the second display; and
    if it is determined that the user has answered that the symptom corresponding to the first node is absent, causing the display to perform the third display of at least the second node in the decision tree.

5. The control method according to claim 1, wherein the plurality of nodes includes one root, the control method further comprising:
    causing the display to perform the second display of the root, the first node, and the second node that is present between the root and the first node in the decision tree.

6. The control method according to claim 1, wherein the second display includes emphasis and enlargement.

7. The control method according to claim 1, wherein the third display includes deletion of display and grayscale display.

8. The control method according to claim 1, further comprising:
counting a number of levels of child nodes that are linked to the first node from the first node to the plurality of leaves; and
causing the display to display the number of levels as a number of remaining questions.

9. The control method according to claim 1, wherein the input includes at least one of a microphone, a keyboard, and a touch panel.

10. The control method according to claim 1, wherein, if it is determined that the user has answered that the symptom corresponding to the first node is present, the second display of the second node that is directly linked to at least the first node in the decision tree includes the second node being displayed with emphasis.

11. The control method according to claim 1, wherein, in the display of the decision tree:
the first node is configured to be displayed in a first manner if the user has answered that the symptom corresponding to the first node is present;
the first node is configured to be displayed in a second manner if the user has answered that the symptom corresponding to the first node is absent;
the first node is configured to be displayed in a third manner if the presented question is asked and the inputted answer is not acquired from the input;
each of the plurality of nodes other than the first node and each of the plurality of leaves for which inputted answers to presented questions are not acquired are displayed in a fourth manner before the presented questions are asked; and
the first manner, the second manner, the third manner, and the fourth manner are different.

12. The control method according to claim 1, further comprising:
causing the display to display the decision tree during a series of questions, the series of questions being asked in search of one piece of information, the decision tree being displayed during the series of questions for suppressing feelings of anxiety or irksomeness of the user to avoid unnecessary searches of the one piece of information as a result of the anxiety or the irksomeness of the user to further avoid an increase in a processing load and a consumption power of the processor.

13. A non-transitory computer-readable recording medium storing a program for causing a processor to execute the control method according to claim 1.

14. The control method according to claim 1, wherein the number of nodes being displayed in the second display is less than the number of nodes being displayed in the first display.

15. The control method according to claim 1, wherein a number of leaves being displayed in the second display is less than a number of leaves being displayed in the first display.

16. A control device that is connected to a display and an input, the input receiving an inputted answer to a presented question, the control device comprising:
a processor; and
a memory, wherein the processor
causes the display to display a decision tree, the decision tree being stored in the memory and including a plurality of nodes and a plurality of leaves, the plurality of nodes each corresponding to a question asking about presence or absence of a corresponding one of a plurality of symptoms, the plurality of leaves each corresponding to one of a plurality of illnesses, and to perform a first display of each of the plurality of nodes at a first time point,
acquires the inputted answer to the presented question from the input, the inputted answer being input to the input by a user,
determines an answer to the presented question from the inputted answer,
if it is determined that the user has answered that a symptom corresponding to a first node is present, causes the display to perform, at a second time point later than the first time point, a second display of a second node that is directly linked to at least the first node in the decision tree and is located in a lower level, wherein a number of nodes being displayed in the second display is different from a number of nodes being displayed in the first display, and
if it is determined that the user has answered that the symptom corresponding to the first node is absent, causes the display to perform the second display of a third node that is directly linked to at least the first node in the decision tree and is located in the lower level, the third node being different from the second node,
wherein, if it is determined that the user's inputted answer is not included in candidate answers to the presented question, the processor further
determines that the inputted answer is included in candidate answers to other questions excluding the presented question from questions included in the decision tree;
registers the user's inputted answer in a keyword list;
changes a display mode of a node, corresponding to the question for which the user's inputted answer has been registered, to a predetermined display mode indicating that a search has been progressed; and
reconstructs the decision tree based on the keyword list and the predetermined display mode by including a fourth node corresponding to the user's inputted answer, the fourth node being different from the first, second, and third nodes.

17. The control device according to claim 16, wherein the number of nodes being displayed in the second display is less than the number of nodes being displayed in the first display.

* * * * *